United States Patent
Bamba et al.

(10) Patent No.: US 9,097,686 B2
(45) Date of Patent: Aug. 4, 2015

(54) OPTICAL TYPE INSPECTION APPARATUS, INSPECTION SYSTEM AND THE WAFER FOR COORDINATES MANAGEMENT

(75) Inventors: Yoshio Bamba, Tokyo (JP); Yukihisa Mohara, Tokyo (JP); Kowa Tabei, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 54 days.

(21) Appl. No.: 14/129,906

(22) PCT Filed: Jun. 22, 2012

(86) PCT No.: PCT/JP2012/065972
§ 371 (c)(1),
(2), (4) Date: Dec. 27, 2013

(87) PCT Pub. No.: WO2013/005582
PCT Pub. Date: Jan. 10, 2013

(65) Prior Publication Data
US 2014/0192352 A1    Jul. 10, 2014

(30) Foreign Application Priority Data

Jul. 6, 2011    (JP) ................................ 2011-150140

(51) Int. Cl.
G01N 21/95        (2006.01)
H01L 21/66        (2006.01)
G01N 21/956       (2006.01)

(52) U.S. Cl.
CPC .......... *G01N 21/9501* (2013.01); *G01N 21/956* (2013.01); *H01L 22/12* (2013.01)

(58) Field of Classification Search
CPC . G01N 21/94; G01N 21/9501; G01N 21/956; H01L 22/12

USPC ........ 356/237.1–237.5, 243.1–243.8; 438/16, 438/18, 460; 257/48, 797
See application file for complete search history.

(56) References Cited

U.S. PATENT DOCUMENTS 7,733,473 B2 *    6/2010    Yamashita et al. ......... 356/237.2
2008/0085588 A1 *    4/2008    Subramanian ................ 438/460
(Continued)

FOREIGN PATENT DOCUMENTS

JP    2010-256340 A    11/2010
JP    2011-075431 A    4/2011

OTHER PUBLICATIONS

International Search Report issued in International Application No. PCT/JP2012/065972 dated Sep. 18, 2012.

*Primary Examiner* — Hoa Pham
(74) *Attorney, Agent, or Firm* — McDermott Will & Emery LLP

(57) ABSTRACT

This optical inspection device has: a line sensor on which channels are arranged; a moving means for moving a wafer mounted on a stage relative to the line sensor; a stage position detection means for detecting the on-stage positions of pseudo-defects in images formed on the channels as pseudo-defect stage coordinates, said coordinate management wafer being a wafer on which one pseudo-defect die is formed per row and column of a matrix of dies and each pseudo-defect die has a plurality of pseudo-defects formed in a line in the columnar direction; a coordinate transformation means for transforming the pseudo-defect stage coordinates into pseudo-defect die coordinates; a difference computation means for computing the differences of the pseudo-defect die coordinates from design coordinates; and a characteristic pattern acquisition means for obtaining a coordinate error characteristic pattern in which the differences from the pseudo-defect stage coordinates increase or decrease along a straight line.

13 Claims, 27 Drawing Sheets

(56) References Cited

U.S. PATENT DOCUMENTS

| | | | |
|---|---|---|---|
| 2009/0304261 A1* | 12/2009 | Takahashi et al. | 382/149 |
| 2011/0304848 A1* | 12/2011 | Tanaka et al. | 356/237.2 |
| 2015/0097272 A1* | 4/2015 | Jang et al. | 257/620 |

* cited by examiner

CORRECTED DEFECT COORDINATE

OPTICAL TYPE INSPECTION APPARATUS, INSPECTION SYSTEM AND THE WAFER FOR COORDINATES MANAGEMENT

RELATED APPLICATIONS

This application is the U.S. National Phase under 35 U.S.C. §371 of International Application No. PCT/JP2012/065972, filed on Jun. 22, 2012, which in turn claims the benefit of Japanese Application No. 2011-150140, filed on Jul. 6, 2011, the disclosures of which Applications are incorporated by reference herein.

TECHNICAL FIELD

The present invention relates to an optical type inspection apparatus, an inspection system including the same, and a wafer for coordinates management used for the same.

BACKGROUND ART

An optical type inspection apparatus is used for inspection of defects generated in a manufacturing process of a display device using a semiconductor device, liquid crystals and the like. Concretely, an optical type inspection apparatus finds defects and obtains the positions of the defects (defect coordinates). An optical type inspection apparatus is provided on an inspection system that is provided with a review device in addition to the optical type inspection apparatus. The review device displays with magnification the periphery of the position that a defect coordinate having been obtained by the optical type inspection apparatus represents, and can display with magnification the defect at the defect coordinate. A manufacturer of a semiconductor device or a display device can determine the cause of the generation of a defect by observing the defect that is displayed with magnification and reduce defects.

The structure of a semiconductor device or a display device is refined for high performance. Accordingly, it is considered that fine defects, which would not have conventionally caused a failure of a semiconductor device or a display device, may cause failures, and such fine defects have come to be an object of inspection by an optical type inspection apparatus. For the purpose of improving the inspection accuracy of an optical type inspection apparatus, a method of correcting the position deviation amount of a stage, on which a semiconductor device or a display device are mounted to be transported, is presented (see Patent Document 1, etc.)

RELATED ART DOCUMENT

Patent Documents

Patent Document 1: Japanese Patent Application Laid-Open No. 2009-10325

DISCLOSURE OF THE INVENTION

Problems to be Solved by the Invention

When defects as inspection objects have become fine, a review device comes to display these fine defects with magnification compared with conventional cases so that these fine defects can be easily observed. Accordingly, an area magnified for display becomes a narrow area only of the vicinity of a defect coordinate. It is considered that when an error is included in a defect coordinate obtained by an optical type inspection apparatus, even if the periphery of the defect coordinate is magnified, there is a case that the defect is not displayed on the display screen.

In this situation, an object to be attained by the present invention is to provide an optical type inspection apparatus capable of reducing error included in a defect coordinate, an inspection system provided with the optical type inspection apparatus, and a wafer for coordinates management used by the optical type inspection apparatus.

Means for Solving the Problem

According to the present invention, provided is an optical type inspection apparatus including a line sensor with plural channels capable of forming an image of a surface of a wafer, the channels being arrayed with equal intervals along Y axis direction, and a transporting unit that forms an image of an entire surface of the wafer on the channels by loading the wafer on a stage and repeatedly transporting, relatively to the line sensor, the wafer along X axis direction perpendicular to the Y axis direction, wherein the optical type inspection apparatus inspects the surface of the wafer, the optical type inspection apparatus including: a stage position detecting unit, wherein, when a wafer for coordinates management has been arranged such that: a matrix is set on the surface; one pseudo defect die is formed on each row of the matrix and one pseudo defect die is formed on each column of the matrix; and plural pseudo defects are formed in the each pseudo defect die in one array along a column direction with equal intervals such that a pitch between formed images, of the pseudo defects, on the channels is the same as a pitch between the channels, and if the wafer for coordinates management has been inspected as the wafer such that the Y axis direction and the column direction are substantially parallel to each other and an image of one pseudo defect is formed on the each channel, corresponding to the each pseudo defect die, then the stage position detecting unit detects a position, on the stage, of the each pseudo defect whose image has been formed on the corresponding channel, as a pseudo defect stage coordinate; a coordinate transforming unit that transforms the each detected pseudo defect stage coordinate into a pseudo defect die coordinate representing a position in the pseudo defect die that includes the pseudo defect; a difference computing unit that computes difference of the each pseudo defect die coordinate from a designed coordinate based on design, wherein the difference is generated when the pseudo defect is formed in the corresponding pseudo defect die; and a characteristic pattern obtaining unit that obtains at least either one of a coordinate error characteristic pattern in which the difference vibrates with a substantially constant amplitude with respect to the pseudo defect stage coordinate and a coordinate error characteristic pattern in which the difference increases or decreases along a line.

Further, according to the invention, provided is an inspection system including the above-described optical type inspection apparatus.

Still further, according to the invention, provided is a wafer for coordinates management, wherein a matrix is set on a surface of the wafer for coordinates management, wherein only one pseudo defect die is formed on each row of the matrix and only one pseudo defect die is formed on each column of the matrix, and wherein plural pseudo defects are formed on the each pseudo defect die with equal intervals only in one array along column direction of the matrix.

Advantages of the Invention

According to the present invention, it is possible to provide an optical type inspection apparatus capable of reducing error included in a defect coordinate, an inspection system provided with the optical type inspection apparatus, and a wafer for coordinates management used by the optical type inspection apparatus.

EMBODIMENT FOR CARRYING OUT THE INVENTION

Figure 1A:
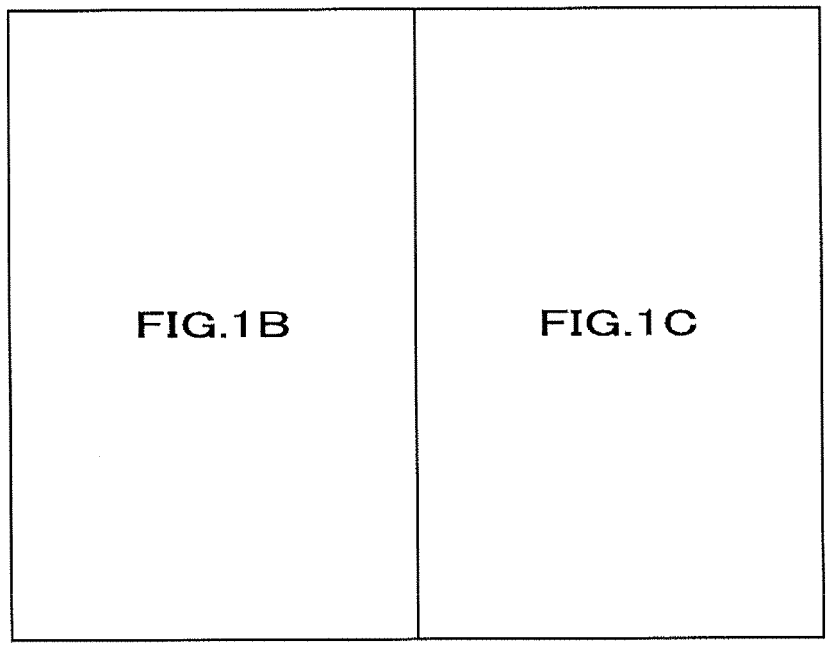
FIGS. 1A to 1C are configuration diagrams of an optical type inspection apparatus in an embodiment according to the present invention.

An embodiment according to the present invention will be described below, referring to the drawings, as appropriate. Incidentally, in the drawings, the same reference symbols will be assigned to elements common to respective drawings, and overlapping description will be omitted.

Figure 1B:
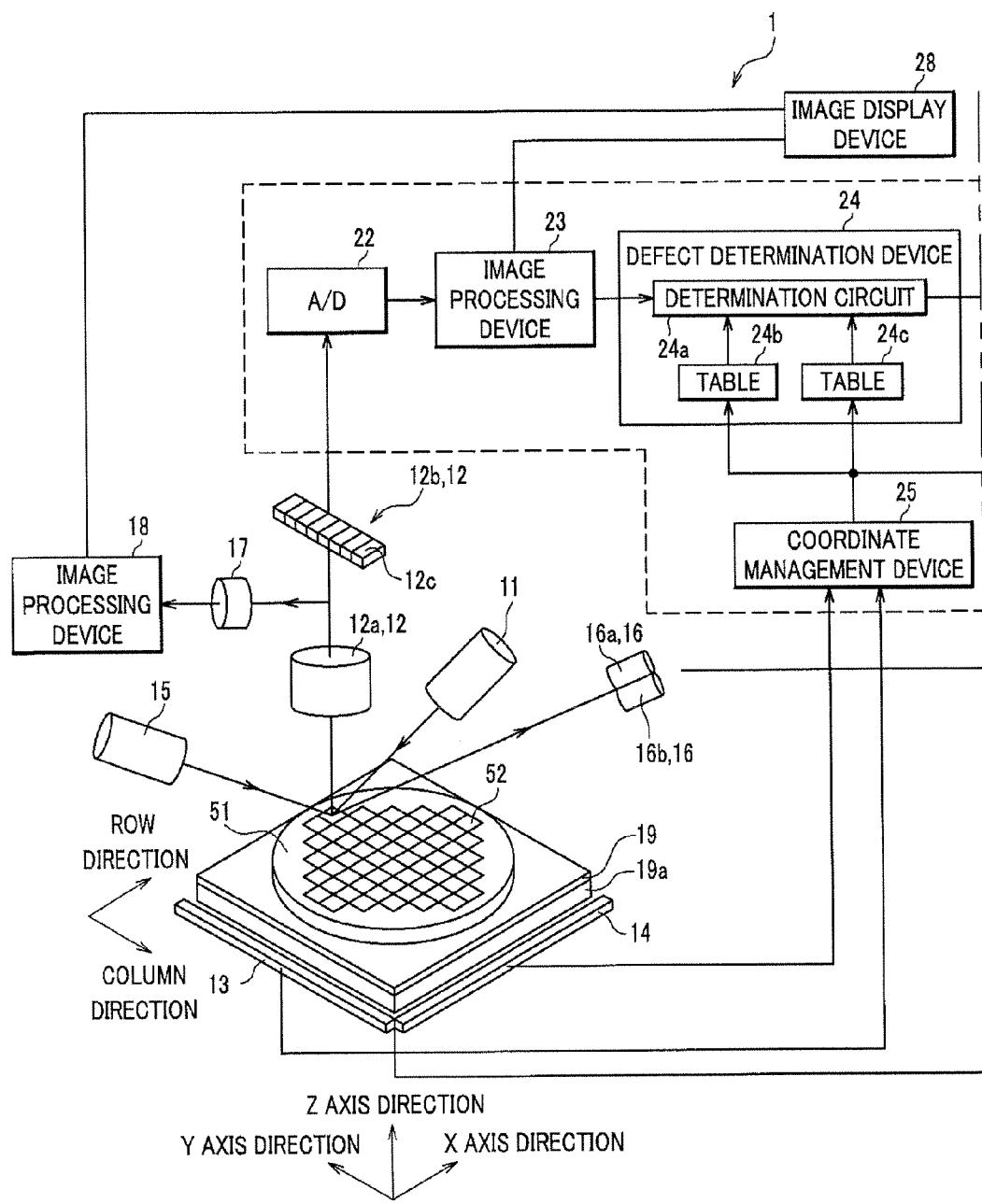
Figure 1C:
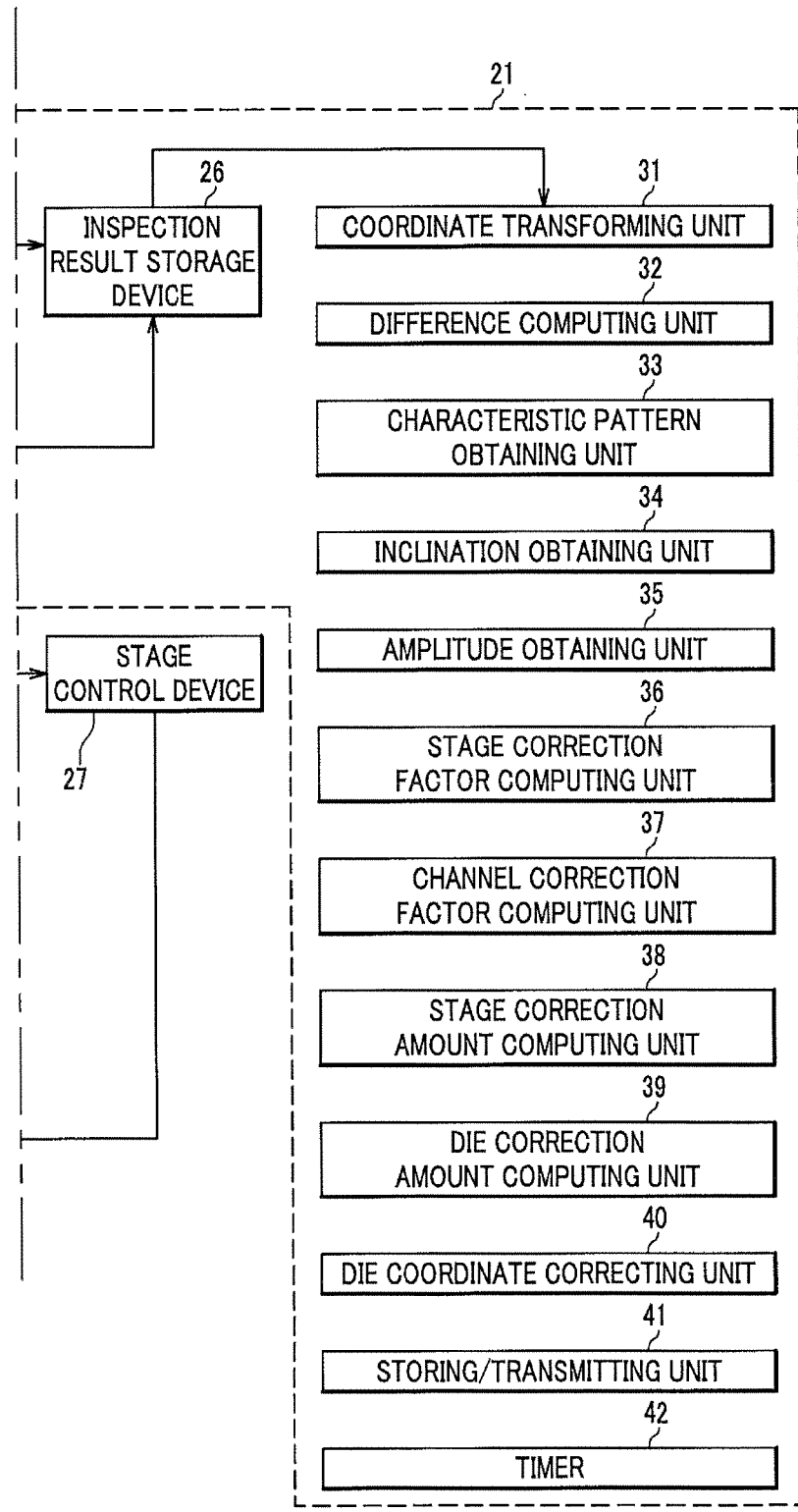

FIGS. 1A to 1C are configuration diagrams of an optical type inspection apparatus 1 in an embodiment according to the present invention. The optical type inspection apparatus 1 includes an optical detection system (11, 12, etc.) detecting defects and a focus control system (15, 16, etc., a focus detection optical system + a focus drive system). During scanning of a wafer for coordinates management (wafer) 51, it is possible to control the focus drive system of the focus control system (15, 16, etc.) to the position of the focal point of the optical detection system (11, 12, etc.) detected by the focus detection optical system of the focus control system (15, 16, etc.) so as to follow the asperity (height) of the surface of the wafer for coordinates management 51.

The optical type inspection apparatus 1 includes a lighting unit 11 of the optical detection system, a detection unit 12 (a photoreceptive unit 12a, an image forming unit (line sensor) 12b) of the optical detection system, a Y scale (stage position detection unit) 13, an X scale (stage position detection unit) 14, a lighting device 15 of the focus control (surface height position detection) system, a detector 16 (16a, 16b, (Each one set is configured by two detectors.)) of the surface height position detection system, an image surface observing unit 17, an image processing device 18, a stage 19, a transporting unit 19a, a processing device 21, a stage control device 27, and an image display device 28.

The lighting unit 11 projects a laser light with a certain wavelength as an inspection light, and irradiates the surface of the wafer for coordinates management 51, which is an inspection object, with the optical beam of the laser light.

The detection unit 12 (12a, 12b) of the defect detection system receives an inspection light reflecting or scattering from the surface of the wafer for coordinates management 51, and thereby detects an optical intensity.

The surface of the wafer for coordinates management 51 is provided with pseudo defect dies (chips) 52. The wafer for coordinates management 51 is stuck to the stage 19, and the stage 19 is transported in Y axis direction and X axis direction by the transporting unit 19a so that an inspection light projected from the lighting unit 11 scans the surface of the wafer for coordinates management (wafer) 51. Thus, it is possible to make the inspection light scan the entire surface of the wafer for coordinates management 51.

As the image forming unit (line sensor) 12b of the detection unit 12 of the defect detection system, for example, a TDI (Time Delay and Integration) sensor, a CCD (Charge Coupled Device) sensor, a photomultiplier, or the like can be used. The photoreceptive unit 12a of the detection unit 12 of the defect detection system forms an image on the image forming unit (line sensor) 12b by receiving/collecting a scattering light, of an inspection light, generated on the surface of the wafer for coordinates management 51. Plural channels 12c are arrayed in Y axis direction on the image forming unit (line sensor) 12b. Positions, the positions being in respective channels 12c, where corresponding scattering lights of the inspection light have been formed can be specified individually for the respective channels 12c. The image forming unit (line sensor) 12b converts the formed images of the scattering lights of the inspection light into the intensities (electrical signals) of the scattering lights at the respective positions in Y axis direction, and outputs the electrical signals to the processing device 21 as image signals.

As the Y scale 13 and the X scale 14, for example, laser scales or the like can be used. The Y scale 13 and the X scale 14 respectively detect the Y axis direction position (stage Y coordinate Ys) and the X axis direction position (stage X coordinate Xs) of the stage 19, and output the position information to the processing device 21. As described above, a wafer for coordinates management (wafer) 51 is mounted on the stage 19, and the stage 19 is transported along Y axis direction and X axis direction by the transporting unit 19a. On the other hand, the optical path of the inspection light is not moved. Accordingly, the irradiation position of the wafer for coordinates management (wafer) 51 on the optical path of the inspection light can be associated with a set of the Y axis direction position (stage Y coordinate Ys) and the X axis direction position (stage X coordinate Xs) of the stage 19 one with one. That is, as the coordinate of an irradiation position, a Y axis direction position (stage Y coordinate Ys) and an X axis direction position (stage X coordinate Xs) of the stage 19 can be used. The stage Y coordinate Ys and the stage X coordinate Xs are transmitted to the coordinate management device (stage position detection unit) 25 of the processing device 21.

The lighting device 15 of the surface height position detection system irradiates the wafer for coordinates management (wafer) 51, which is an inspection object, with an inspection light for detecting a surface height position. The detector 16 (16a, 16b) of the surface height position detection system detects the surface height position of the wafer for coordinates management (wafer) 51. The detector 16 (16a, 16b) includes two detectors 16a, 16b. These two detectors 16a, 16b have different detection central positions with respect to the upper/lower direction (Z axis direction) of an inspection object, and can detect (determine) the high/low relative to a predetermined height.

As the image surface observing unit 17, a TTL (Through the Lens) method can be adopted, wherein, for example, a CCD sensor can be used. The image surface observing unit 17 receives a flattering light, of an inspection light, having passed through the photoreceptive unit 12a and been collected, and converts the intensity of the received light into an electrical signal. The converted electrical signal is output to the image processing device 18 as an image signal.

The processing device 21 includes an A/D convertor 22, an image processing device 23, a defect determination device 24, a coordinate management device 25, and an inspection result storage device 26.

The A/D convertor 22 converts an image signal of an analog signal having been input from the image forming unit (line sensor) 12b into an image signal of a digital signal and outputs the converted image signal.

The image processing device 23 includes, for example, a delay circuit and a difference detection circuit. The delay circuit delays an image signal having been input from the A/D convertor 22. The delay circuit outputs image signals of a chip on which irradiation with an inspection light has already been terminated, wherein the chip is immediately before a pseudo defect die (chip) 52 that is currently irradiated. The difference detection circuit detects a difference between an image signal of the pseudo defect die (chip) 52 which is currently irradiated with an inspection light, the image signal being directly input from the A/D convertor 22, and an image signal, the signal being input via the delay circuit, of the chip on which irradiation with an inspection light has been terminated immediately before.

The defect determination device 24 inspects (determines) whether or not defect (pseudo defect) exists in a pseudo defect die currently irradiated with the inspection light, from the difference in image signal, the difference having been detected by the image processing device 23. The defect determination device 24 includes a determination circuit 24a and factor tables (tables) 24b and 24c. The factor tables 24b, 24c store factors for changing a threshold value for defect determination, associating the factors with coordinate information. Coordinate information (stage Y coordinate Ys, stage X coordinate Xs) are input from a stage position detection unit (coordinate management device) 25, and the factor tables 24b, 24c output factors stored in association with this coordinate information to the determination circuit 24a. A difference in image signal is input from the image processing device 23 to the determination circuit 24a, and factors for changing a threshold are input from the factor tables 24b and 24c. The determination circuit 24a multiplies a predetermined value by a factor for changing a threshold value, and thereby computes a threshold value. Then, the determination circuit 24a compares the difference in image signal and the threshold value, and if the difference in image signal is greater than or equal to the threshold value, the determination circuit 24a determines that there is a defect, and if the difference in image signal is smaller than the threshold value, the determination circuit 24a determines that there is no defect. This determination result is output to the inspection result storage device 26. The determination circuit 24a outputs the information of the threshold value used for the determination to the inspection result storage device 26.

The coordinate management device 25 determines the position (stage Y coordinate Ys and stage X coordinate Xs) where a light beam is currently projected, based on position information having been input from the Y scale 13 and the X scale 14.

When the defect determination device 24 has determined that there is a defect, the inspection result storage device 26 stores the coordinate information (stage Y coordinate Ys and stage X coordinate Xs) having been input from the coordinate management device 25 as pseudo defect stage coordinate (pseudo defect stage Y coordinate Ys0 and pseudo defect stage X coordinate Xs0). The inspection result storage device 26 stores information of the value having been input from the defect determination device 24, associating the information with the coordinate information.

The stage control device 27 controls the transporting unit 19*a*, thereby transports the stage 19 upward or downward (transports along Z axis direction), and thus sets the focal point of the optical system of the detection unit 12 onto the surface of the wafer for coordinates management 51. Further, the stage control device 27 controls the transporting unit 19*a*, thereby transports the stage 19 along X axis direction and Y axis direction, and thus makes an inspection light scan the entire surface of the wafer for coordinates management 51.

The processing device 21 includes a coordinate transforming unit 31, a difference computing unit 32, a characteristic pattern obtaining unit 33, an inclination obtaining unit 34, an amplitude obtaining unit 35, a stage correction factor computing unit 36, a cannel correction factor computing unit 37, a stage correction amount computing unit 38, a die correction amount computing unit 39, a die coordinate correcting unit 40, a storing/transmitting unit 41, and a timer 42. The functions of the respective units will be described in the description of a method of correcting defect coordinate using the later-described optical type inspection apparatus 1.

Figure 2:
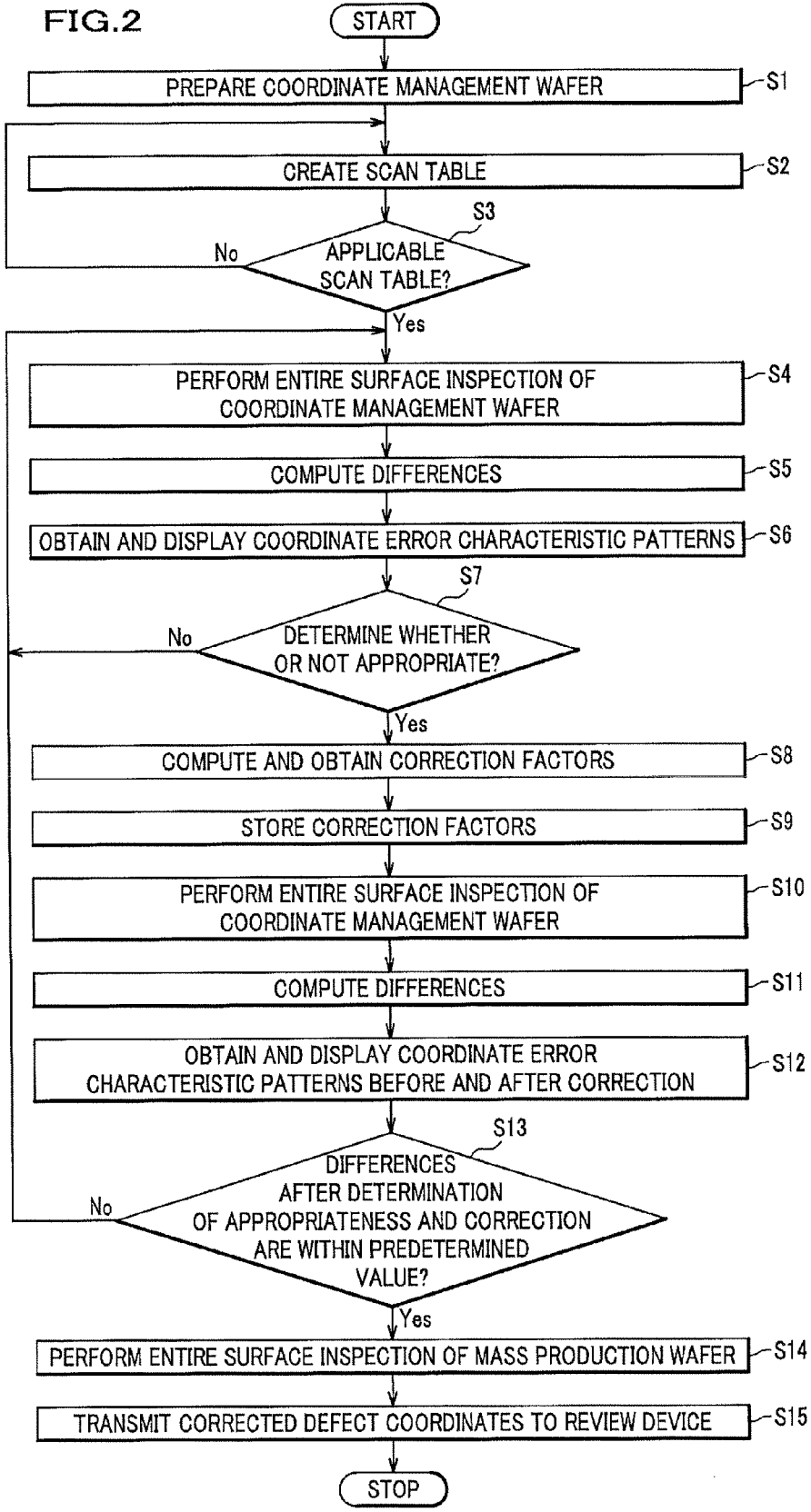
FIG. 2 is a flowchart of a method of correcting a defect coordinate, using the optical type inspection apparatus in the embodiment according to the present invention.

FIG. 2 shows a flowchart of a method of correcting defect coordinate, using the optical type inspection apparatus 1 in the embodiment according to the present invention.

Figure 3:
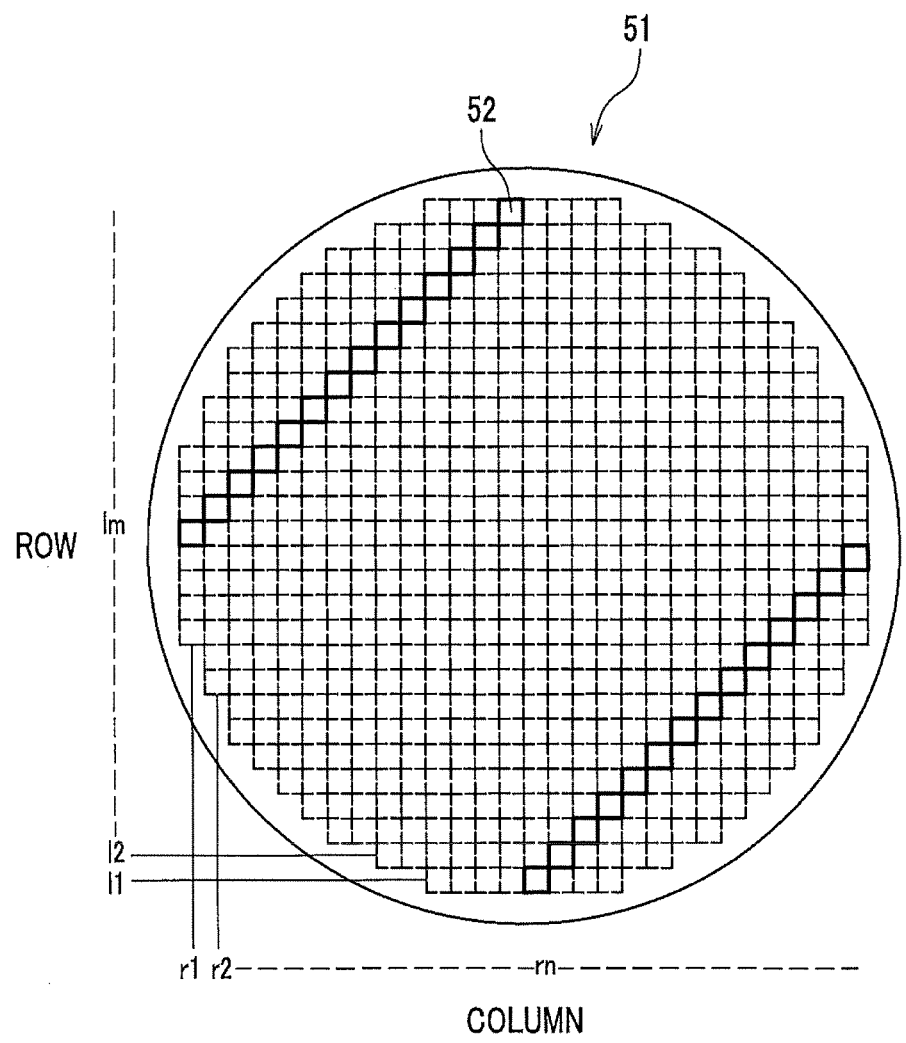
FIG. 3 is a plan view of a wafer for coordinates management in the embodiment according to the present invention.

First, in step S1, an operator or the like of the optical type inspection apparatus 1 prepares a wafer for coordinates management 51. FIG. 3 is a plan view of the prepared wafer for coordinates management 51. A matrix is set on the surface of the wafer for coordinates management 51. In the matrix, plural rows l1, l2, . . . , lm, . . . are set, and plural columns r1, r2, . . . rn, . . . are set. One pseudo defect die 52 is formed on each line l1, l2, . . . , lm, . . . . Likewise, one pseudo defect die 52 is formed on each column on each column r1, r2, . . . rn, . . . .

Figure 4:
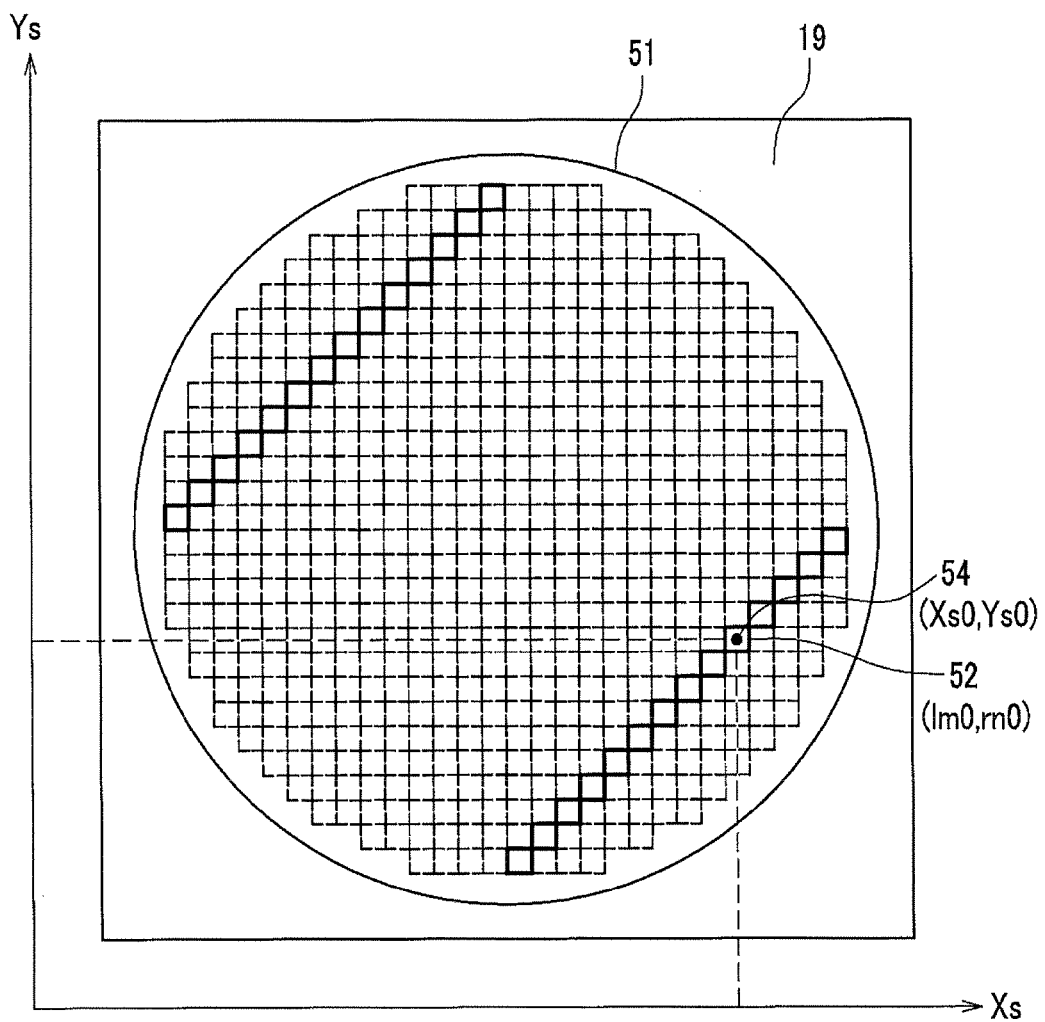
FIG. 4 is a diagram for illustration of relationship between a stage coordinate and a pseudo defect stage coordinate on a wafer for coordinates management in the embodiment according to the present invention, wherein a wafer for coordinates management fixed on a stage is shown.

FIG. 4 shows the wafer for coordinates management 51 fixed on the stage 19. Pseudo defect dies 52 are formed on the wafer for coordinates management 51, and pseudo defects 54 are formed in the pseudo defect dies 52. Incidentally, although plural pseudo defects 54 are formed in a pseudo defect die 52, only one pseudo defect 54 is shown in a certain pseudo defect die 52 for easy understanding in FIG. 4. When rows and columns are set on the wafer for coordinates management 51, a position (lm0, rn0) of a pseudo defect die 52 can be defined by setting a certain row lm0 and a certain column rn0. Based on a designed coordinate (on the die coordinate) in the pseudo defect die 52 and the position (lm0, rn0) of the pseudo defect die 52, it is possible to determine the position forming a pseudo defect 54, and form the pseudo defect 54. Incidentally, as described later, a pseudo defect 54 formed in such a manner is determined to be a defect by the defect determination device 24 in FIGS. 1A to 1C, and the pseudo detect stage coordinate (the pseudo detect stage Y coordinate Ys0 and the pseudo defect stage X coordinate Xs0) is stored in the inspection result storage device 26, as a position where the pseudo defect 54 is located on the stage coordinate (stage Y coordinate Ys and the stage X coordinate Xs).

Figure 5:
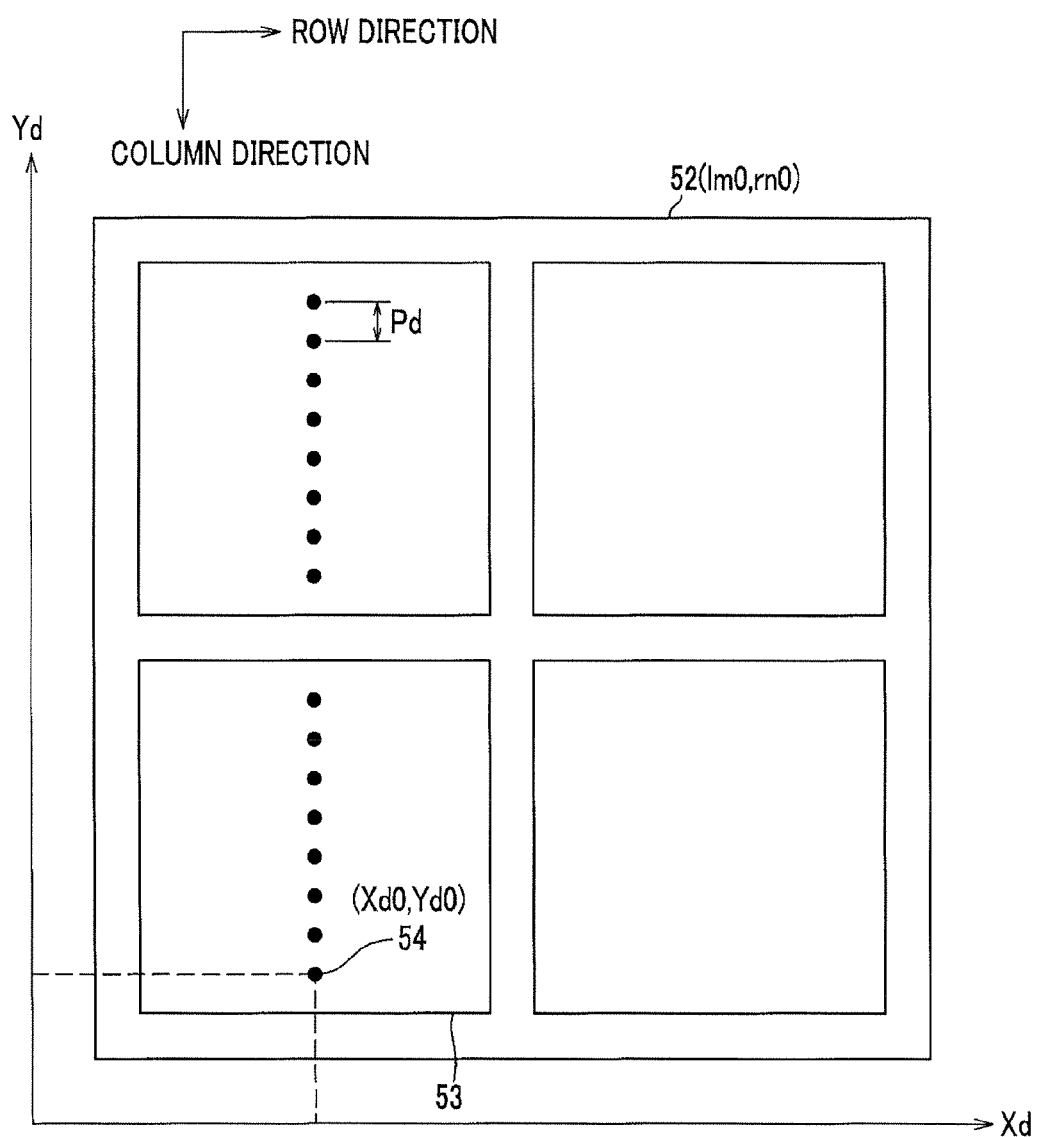
FIG. 5 is a diagram for illustration of the relationship between the die coordinate of a pseudo defect die formed on the wafer for coordinates management in the embodiment according to the present invention and a pseudo defect die coordinate, showing a plan view of the pseudo defect die.

FIG. 5 shows a plan view of a pseudo defect dies 52. Die cells 53 are formed in the pseudo defect die 52. In the example in FIG. 5, die cells 53, totally four in two vertical and horizontal rows, are formed. In the die cells 53, plural (totally 16 defects, in the example in FIG. 5, eight for each) pseudo defects 54 are formed. Plural pseudo defects 54 are disposed on one column in the column direction (Y axis direction) of the matrix. Further, the plural pseudo defects 54 are formed such as to have equal intervals of pitch Pd. That is, design is made such that the die X coordinates Xd are equal to each other among plural pseudo defects 54 on the die coordinate (die Y coordinate Ys and die X coordinate Xd), which is the coordinate in the pseudo defect die 52. Further, the die Y coordinates Yd of the designed coordinate are designed such as to have a constant interval (pitch Pd) between adjacent pseudo defects 54. Incidentally, as shown in FIG. 4, the stage coordinates (stage Y coordinate Ys and stage X coordinates Xs) of the formed pseudo defects 54 are stored in the inspection result storage device 26 as pseudo defect stage coordinates (pseudo defect stage Y coordinate Ys0 and pseudo defect stage X coordinate Xs0). Such a pseudo defect stage coordinate (pseudo defect stage Y coordinate Ys0 and pseudo defect stage X coordinate Xs0) can be transferred with one to one relationship into a pseudo defect die coordinate (pseudo defect die X coordinate Xd0 and pseudo defect die Y coordinate Yd0) in the die coordinate (die Y coordinate Yd and die X coordinate Xd). If the pseudo defect stage coordinate (pseudo defect stage Y coordinate Ys0 and pseudo defect stage X coordinate Xs0) includes an error, it means that the transferred pseudo defect die coordinate (pseudo defect die X coordinate Xd0 and pseudo defect die Y coordinate Yd0) also includes an error, and does not agree with the above-described designed coordinate, which causes a difference. In the present embodiment, as the difference can be used to correct the defect coordinate of a real defect, a defect coordinate can be obtained with high accuracy.

Returning to FIG. 2, in step S2 in FIG. 2, the operator (the manufacturer of semiconductor devices or display devices) of the optical type inspection apparatus 1 creates a scan table (inspection recipe) used in using the wafer for coordinates management 51. By the scan table, a scan method (scan path along Y axis direction and X axis direction) of the inspection light onto the wafer for coordinates management 51 is determined. The scan table refers to a buffer that stores in advance a moving path for moving the transporting unit 19*a* by the stage control device 27, as the scan path. Incidentally, in scanning with the inspection light, as the position relationship between the optical path of the inspection light and the line sensor 12*b* is unchanged, it is also possible to consider that the line sensor 12*b* performs this scanning.

Figure 6:
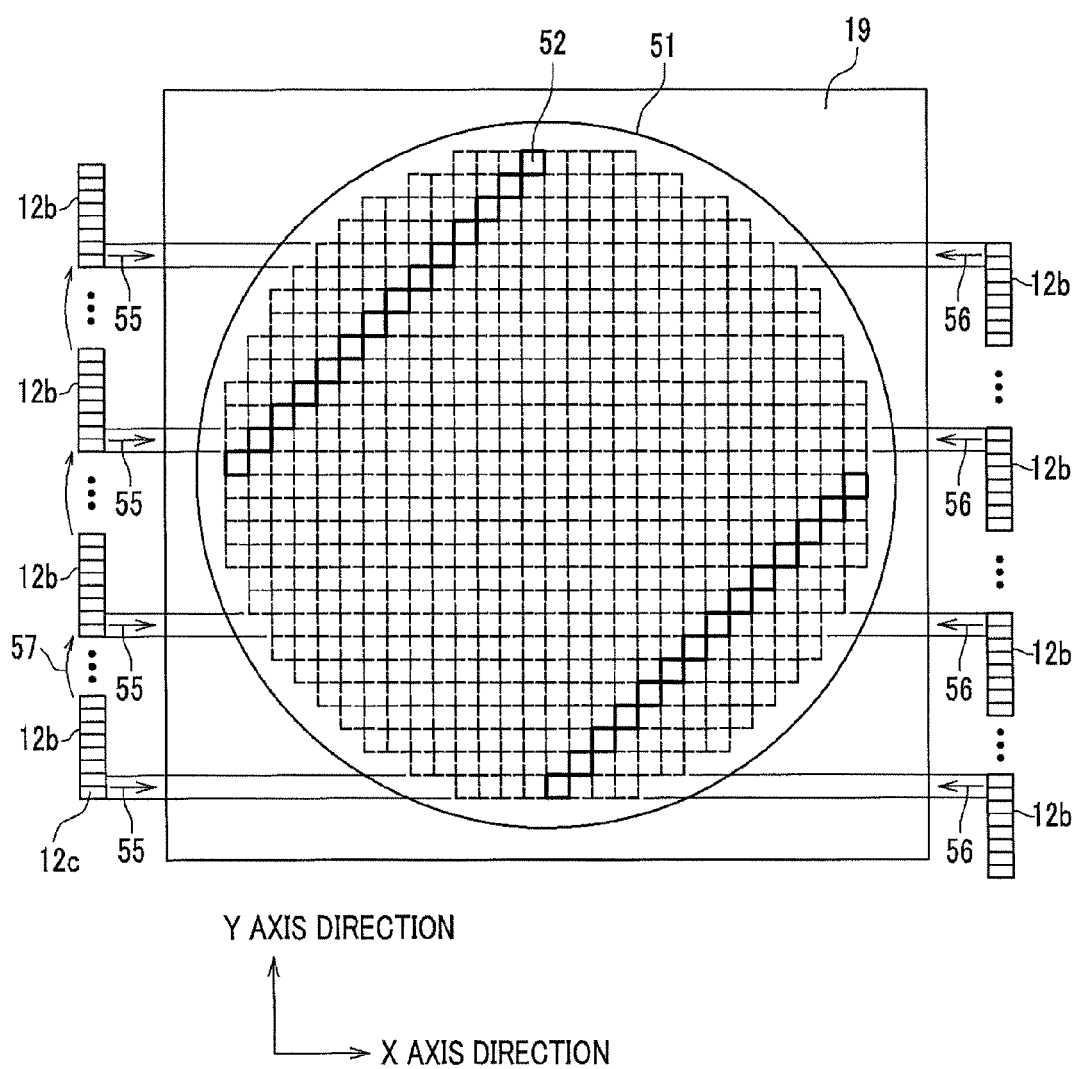
FIG. 6 is a diagram for illustration of a method of scanning by a line sensor relative to a wafer for coordinates management.

FIG. 6 shows a method of relative scanning of the wafer for coordinates management 51 by the line sensor 12*b*. In case that the line sensor 12*b* performs so-called forward scanning 55 that is scanning along X axis direction from the left to the right in FIG. 6, the line sensor 12*b* scans, setting the lowermost portion with respect to Y axis direction of the line sensor 12*b* in FIG. 6 to the lowermost portion with respect to Y axis direction of the pseudo defect die 52 in FIG. 6. In case that the line sensor 12*b* performs so-called reverse scanning 56 that is scanning along X axis direction from the right to the left in FIG. 6, the line sensor 12*b* scans, setting the uppermost portion with respect to Y axis direction of the line sensor 12*b* in FIG. 6 to the uppermost portion with respect to Y axis direction of the pseudo defect die 52 in FIG. 6. The forward scanning 55 and the reverse scanning 56 are performed on every row where a pseudo defect die (chips) 52 is arranged. By moving up a row for performing the forward scanning 55 and the reverse scanning 56 one by one to an upper row in FIG. 6, it is possible to scan all pseudo defect dies 52 on the wafer for coordinates management 51 by the line sensor 12*b*. Incidentally, it is not necessarily required to perform both the forward scanning 55 and the reverse scanning 56, and either one may be performed. Further, rows for performing the forward scanning 55 and rows for performing the reverse scanning 56 may be set. Still further, as the wafer for coordinates management 51 is in a circular shape, chipping off may occur on some pseudo defect dies 52 formed at the outer circumferential portion of the wafer for coordinates management 51. Pseudo defects 54, on the upper side or the lower side of FIG. 5, of these pseudo defect dies 52 may be lost by this chipping off. The scan table is produced such that scanning is not performed above pseudo defect dies (incomplete dies) 52 whose pseudo defects 54 are totally or partially missing.

Figure 7:
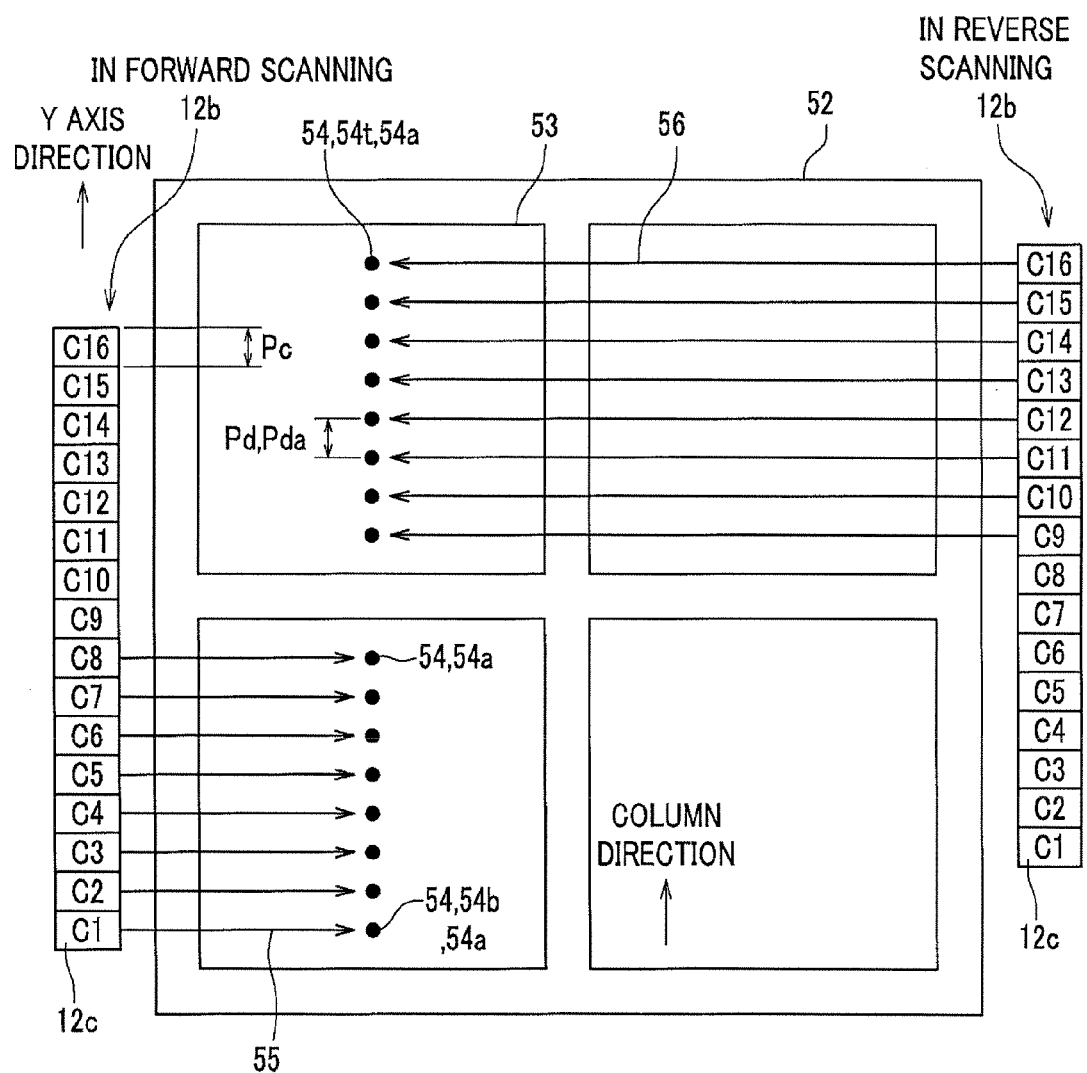
FIG. 7 is a diagram showing the position relationship between formed images of pseudo defects (pseudo defect die) on channels and the channels during scanning.

FIG. 7 shows the position relationship between formed images, of pseudo defects 54, on channels 12c and the channels 12c during scanning. In the present embodiment, as errors in position coordinates of pseudo defects 54 are taken as the problem, it is necessary to accurately detect the pseudo defect stage coordinates (pseudo defect stage Y coordinate Ys0 and pseudo defect stage X coordinate Xs0) of the pseudo defects 54. Accordingly, design is made such that the formed images 54a of pseudo defects 54 on channels 12c are generated at the centers of the width along Y axis direction of the respective channels 12c. In order that the formed images 54a of pseudo defects 54 on channels 12c are generated at the centers of the width along Y axis direction of plural respective channels 12c, it is necessary to make the pitch Pda of the formed images 54a, on the channels 12c, of the pseudo defects 54 equal to the pitch Pc of the channels 12c (Pda=Pc). The pitch Pd of pseudo defects 54 is designed such as to satisfy this condition in preparing the wafer for coordinates management 51 in step S1 in FIG. 2.

However, as shown in FIG. 7, there is a case that, between die cells 53 (between the eighth and ninth pseudo defects 54 from the bottom), a pitch Pd between pseudo defects 54 is different from other pitches Pd. In such a case, for forward scanning, by arranging the channel 12c (C1) at the lower end in FIG. 7 and the formed image 54a of the pseudo defect 54b at the lower end at the same position, it is possible to recognize the formed images 54a of pseudo defects 54, at the centers of the width along Y axis direction of the channels 12c (C1-C8). However, it is understood that the formed images 54a of pseudo defects 54 cannot necessarily be recognized at the centers of the width along Y axis direction of the channels 12c (C9-C16) due to the deviation of pitch Pd.

On the other hand, for reverse scanning, by arranging the channel 12c (C16) at the upper end in FIG. 7 and the formed image 54a of the pseudo defect 54t at the upper end at the same position, it is possible to recognize the formed images 54a of pseudo defects 54, at the centers of the width along Y axis direction of the channels 12c (C9-C16). However, it is understood that the formed images 54a of pseudo defects 54 cannot necessarily be recognized at the centers along the width along Y axis direction of the channels 12c (C1-C8) due to the deviation of pitch Pd.

In this situation, by recognizing the formed images 54a of pseudo defects 54 by the channels 12c (C1-C8) in forward scanning and recognizing the formed images 54a of pseudo defects 54 by the channels 12c (C9-C16) in reverse scanning, it is possible to recognize the formed images 54a of all the pseudo defects 54 at the centers of the width along Y axis direction of the channels 12c (C1-C16). Accordingly, a scan table is set such that the channels 12c (C1-C8) are valid and the channels 12c (C9-C16) are invalid for forward scanning. The scan table is set such that the channels 12c (C9-C16) are valid and the channels 12c (C1-C8) are invalid for reverse scanning. Incidentally, FIG. 7 shows a case that two die cells 53 are arranged along Y axis direction of the pseudo defect die 52. In case that three or more die cells 53 are arranged, the scan table can be set such that the formed images 54a of the pseudo defects 54 in the die cell 53 located at the lower end of these die cells 53 are recognized at the centers of the width along Y axis direction of the channels 12c (C1-C16) in forward scanning, and the formed images 54a of the pseudo defects 54 in the die cell 53 located at the upper end of these die cells 53 are recognized at the centers of the width along Y axis direction of the channels 12c (C1-C16) in reverse scanning. According to these, on a column of pseudo defects 54 in a pseudo defect die 52, the pseudo defect 54b and the pseudo defect 54t located at the both ends can be recognized at the centers of the width along Y axis direction of the channels C1 and C16 (12c).

Subsequently, returning to FIG. 2, in step S3 in FIG. 2, the processing device 21 or the stage control device 27 of the optical type inspection apparatus 1, or the operator determines whether or not a created scan table is applicable. Concretely, by performing inspection, using the created scan table, it is determined whether or not all pseudo defect dies 52 in the wafer for coordinates management 51 can be inspected. Further, by performing inspection, using the created scan table, it is determined whether or not pseudo defects 54 can be detected by all channels 12c in the line sensor 12b. If the scan table has been determined applicable (step S3, Yes), the process proceeds to step S4, and if determined inapplicable (step S3, No), the process returns to step S2.

Subsequently, in step S4, the optical type inspection apparatus 1 performs inspection of the entire surface of the wafer for coordinates management 51, using the scan table created in step S2. In the inspection of the entire surface, first, a later-described correction factor is initialized to be set to zero. Thus, it is possible to obtain a defect coordinate including an error without correcting the defect coordinate. All pseudo defects 54 in the wafer for coordinates management 51 and the pseudo defect dies 52 are detected, and the pseudo defect stage coordinates (pseudo defect stage X coordinate Xs0, pseudo defect state Y coordinate Ys0) of positions, where these pseudo defects 54 have been detected, are detected by the scale position detecting units (Y scale, X scale, and coordinate management device) 13, 14, and 25 (see FIGS. 1A to 1C). The coordinate transforming unit 31 (see FIGS. 1A to 1C) transforms the detected pseudo defect stage coordinates (pseudo defect stage X coordinate Xs0, pseudo defect state Y coordinate Ys0) into pseudo defect die coordinates (pseudo defect die X coordinate Xd0, pseudo defect die Y coordinate Yd0) representing the positions in the pseudo defect dies 52 in which corresponding pseudo defects 54 are included. The storing/transmitting unit 41 (see FIGS. 1A to 1C) stores the pseudo defect stage coordinates (pseudo defect stage X coordinate Xs0, pseudo defect stage Y coordinate Ys0) and the pseudo defect die coordinates (pseudo defect die X coordinate Xd0, pseudo defect die Y coordinate Yd0).

Subsequently, in step S5, the difference computing unit 32 (see FIGS. 1A to 1C) computes differences $\Delta X$ (=Xd0−Xd2), $\Delta Y$ (=Yd0−Yd2) of the pseudo defect die coordinates (pseudo defect die X coordinate Xd0, pseudo defect die Y coordinate Yd0) from designed coordinates (designed X coordinate Xd2, designed Y coordinate Yd2) which are based on design, wherein the differences $\Delta X$ and $\Delta Y$ are generated when the pseudo defects 54 are formed in the pseudo defect dies 52.

Then, in step S6, the characteristic pattern obtaining unit 33 (see FIGS. 1A to 1C) obtains and displays coordinate error characteristic patterns. Before describing the coordinate error characteristic patterns, five kinds of errors that can be detected using the coordinate error characteristic patterns and decrease the accuracy of a defect coordinate, which are (1) inclination error, (2) magnification ratio error, (3) X scale error, (4) Y scale error, and (5) orthogonal degree error, will be described.

(1) Inclination Error

Figure 8:
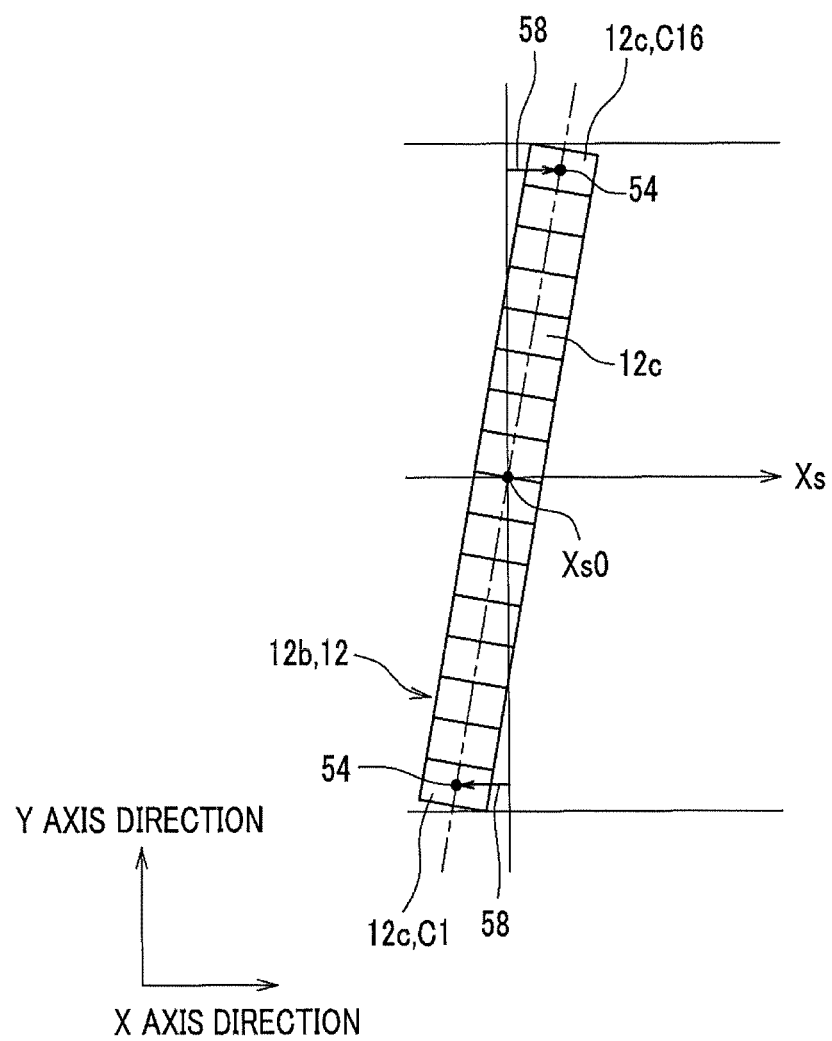
FIG. 8 is a diagram for illustration of errors caused by inclination (inclination error) of a line sensor (No. 1: a diagram showing that a pseudo defect stage coordinate detected by channels C1 and C16 is Xs0)
Figure 9A:
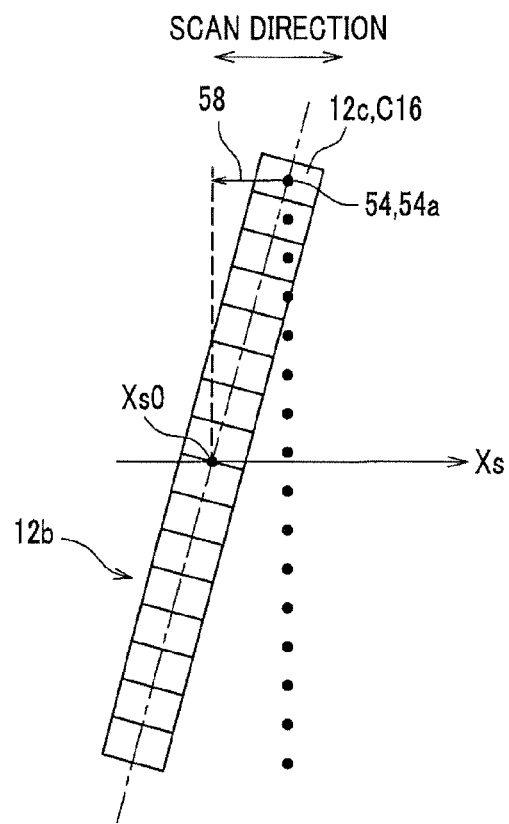
FIG. 9A is a diagram for illustration of inclination errors (No. 2: a diagram showing that a pseudo defect stage coordinate detected by the channel C16 is Xs0)
Figure 9B:
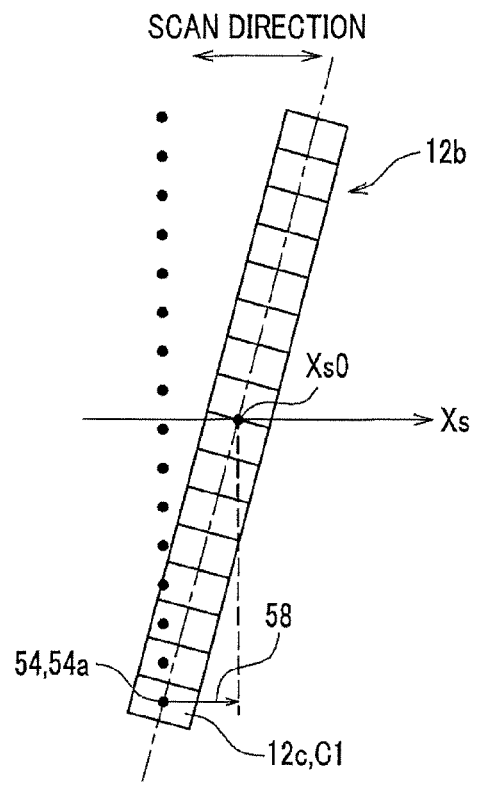
FIG. 9B is a diagram for illustration of inclination errors (No. 3: a diagram showing that a pseudo defect stage coordinate detected by the channel C1 is Xs0)

Using FIG. 8, FIG. 9A, and 9B, an inclination error 58, which is generated by inclination of the line sensor 12b, will be described. In FIG. 8, ideally, the line sensor 12b should be disposed such that the array direction of the channels 12c is parallel to Y axis direction, however, the array direction of the channels 12c is inclined from Y axis direction by an assembling error or a temporal change, to cause inclination errors 58. Concretely, it is assumed that the line sensor 12b is scanning along X axis direction relative to pseudo defects 54 (the wafer for coordinates management 51 (see FIGS. 1A to 1C)). As shown in FIG. 8 and FIG. 9A, when a pseudo defect 54 (the formed image 54a of a pseudo defect) is detected by the channel 12c (C16), a pseudo defect stage coordinate Xs0 is detected with respect to stage X coordinate Xs, as the position of the pseudo defect 54. That is, it is recognized that an inclination error 58 is generated as an error at the position (stage X coordinate Xs) of the pseudo defect 54. Further, it is recognized that the outer on the line sensor 12b, the larger the inclination error 58. FIG. 8 and FIG. 9B show that a pseudo defect 54 (the formed image 54a of a pseudo defect) is detected by the channel 12c (C1). As the stage X coordinate Xs then of the pseudo defect 54 is detected to be a pseudo defect stage coordinate Xs0, it is recognized that an inclination error 58 is generated. Inclination errors 58 are generated in X axis direction.

(2) Magnification Ratio Error

Figure 10:
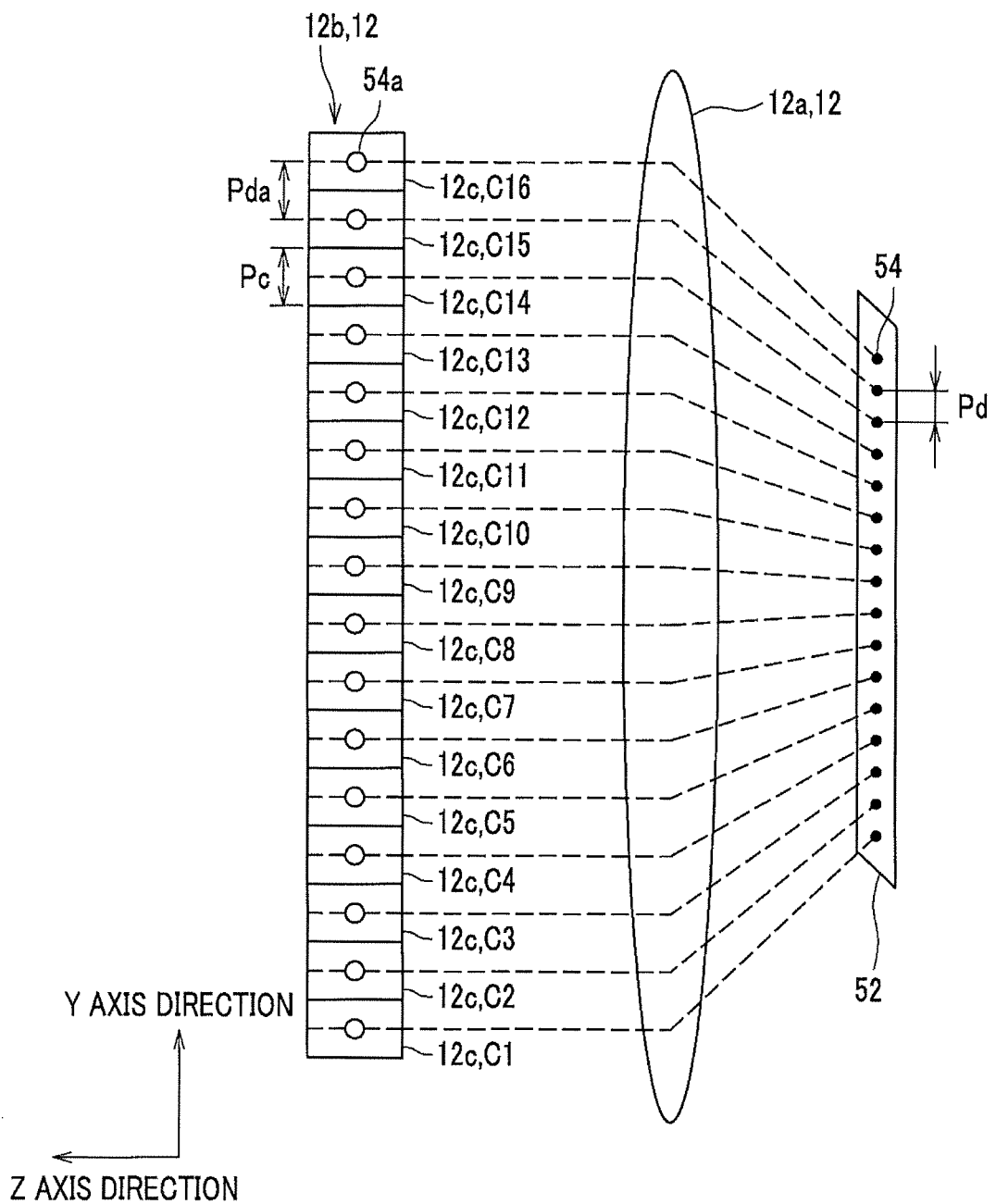
FIG. 10 is a diagram for illustration of errors (magnification ratio errors) in forming images of pseudo defects onto a line sensor (No. 1: a case where magnification ratio errors exist)

Using FIG. 10 and FIG. 11, a magnification ratio error 59 generated on a formed image 54a, of a pseudo defect 54, formed on the line sensor 12b will be described. As shown in FIG. 10, as the photoreceptive unit 12a (see FIGS. 1A to 1C) functions as a collective lens, pseudo defects 54 formed on a pseudo defect die 52 are ideally formed (54a) at the centers of the channels 12c (C1-C16) of the line sensor 12b, and magnification ratio errors 59 (see FIG. 11) are not generated. This is because the pitch Pd of pseudo defects 54 is designed such that the pitch Pc of the channels 12c becomes equal to the pitch Pda of the formed images 54a of pseudo defects 54 (Pc =Pda) in producing a wafer for coordinates management in step S1 in FIG. 2.

Figure 11:
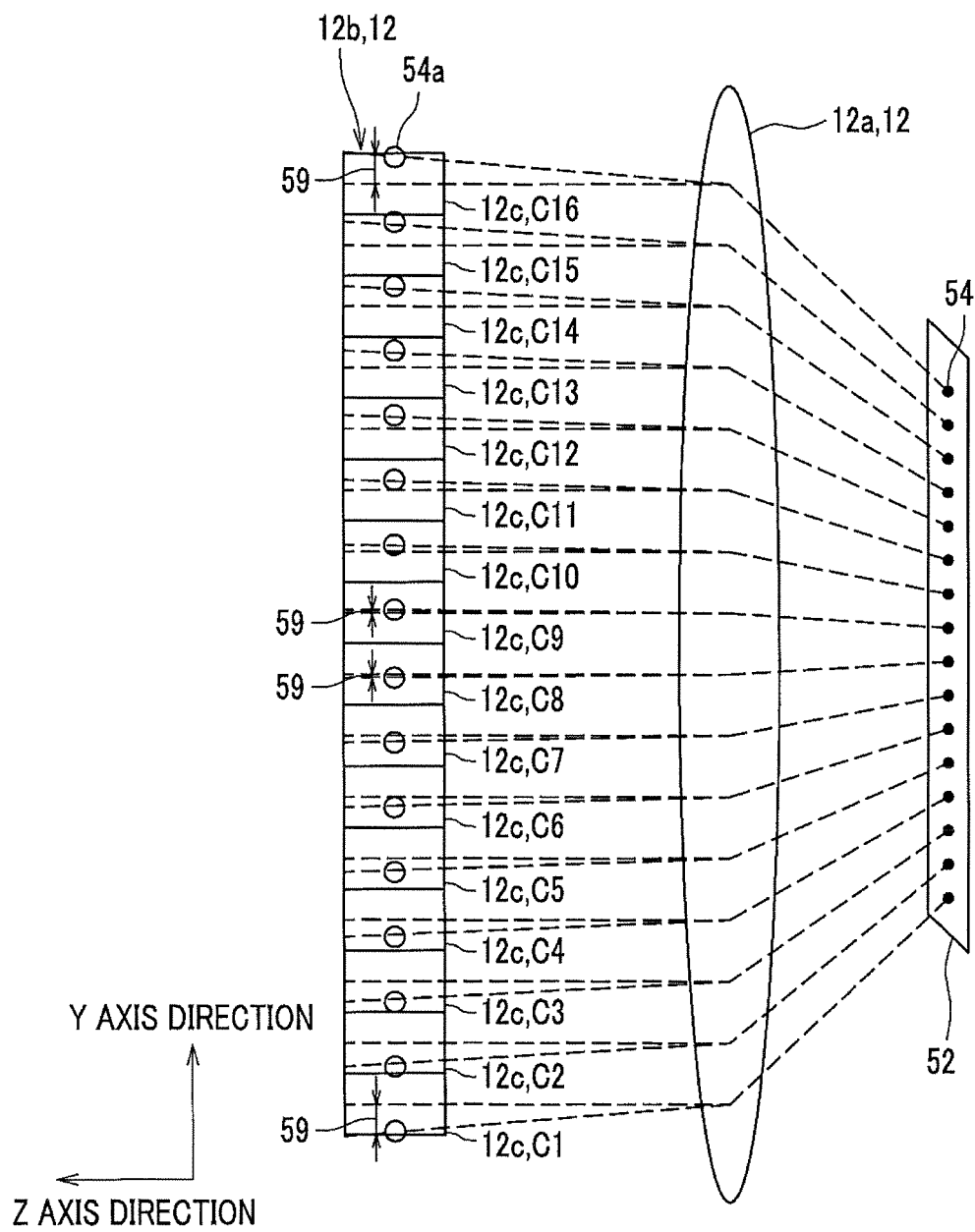
FIG. 11 is a diagram for illustration of errors (magnification ratio errors) in forming images of pseudo defects onto a line sensor (No. 2: a case where magnification ratio error does not exist)

FIG. 11 shows a case that magnification ratio errors 59 are generated. For example, if the distances between the pseudo defect die 52 (pseudo defects 54), the photoreceptive unit 12a, and the line sensor 12b change, the magnification ratio of the formed images 54a of the pseudo defects 54 changes. The formed images 54a of the pseudo defects 54 deviate from the centers of the channels 12c (C1-C16) of the line sensor 12b to generate the magnification ratio errors 59. The magnification ratio errors 59 are generated along Y axis direction, differently from the case of inclination errors 58. It is recognized that the outer on the line sensor 12b, the larger the magnification ratio error 59.

(3) X Scale Error

Figure 12:
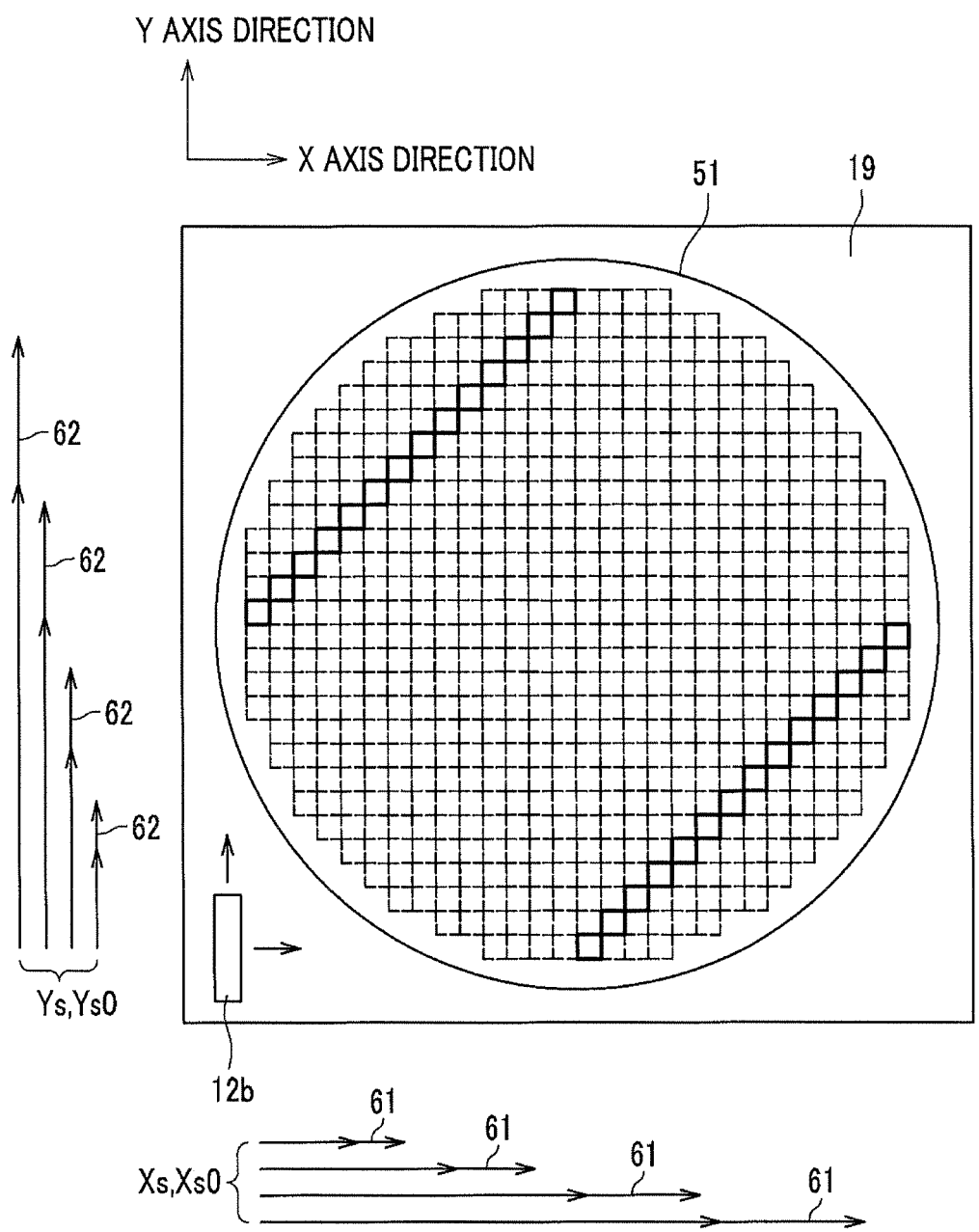
FIG. 12 is a diagram for illustration of errors in transportation amount of a stage (scale errors)

Using FIG. 12, X scale errors 61, which are errors in transportation amount along X axis direction of the stage 19, will be described. A transportation amount along X axis direction is a relative movement amount between the line sensor 12b and the stage 19. An X scale error 61 is generated on a transportation amount (from the coordinate origin) along X axis direction of the stage 19, namely, a stage X coordinate Xs (pseudo defect stage X coordinate Xs0). An X scale error 61 is generated along X axis direction. The larger the transportation amount (stage X coordinate Xs (pseudo defect stage X coordinate Xs0)) along X axis direction of the stage 19 (from the coordinate origin), the larger the X scale error 61. Incidentally, there are cases where an X scale error 61 is generated in a direction that increases a stage X coordinate Xs (pseudo defect stage X coordinate Xs0) (increases a transportation amount), and there are also cases where an X scale error 61 is generated in an opposite direction that decreases a stage X coordinate Xs.

(4) Y Scale Error

Using FIG. 12, Y scale errors 62, which are errors in transportation amount along Y axis direction of the stage 19, will be described. A transportation amount along Y axis direction is a relative movement amount between the line sensor 12b and the stage 19. A Y scale error 62 is generated on a transportation amount (from the coordinate origin) of the stage 19 along Y axis direction, namely, a stage Y coordinate Ys (pseudo defect stage Y coordinate Ys0). A Y scale error 62 is generated along Y axis direction. The larger the transportation amount (stage Y coordinate Ys (pseudo defect stage Y coordinate Ys0)) along Y axis direction of the stage 19 (from the coordinate origin), the larger the Y scale error 62. Incidentally, there are cases where a Y scale error 62 is generated in a direction that increases a stage Y coordinate Ys (pseudo defect stage Y coordinate Ys0) (increases a transportation amount), and there are also cases where an Y scale error 62 is generated in an opposite direction that decreases a stage Y coordinate Ys.

(5) Orthogonal Degree Error

Figure 13:
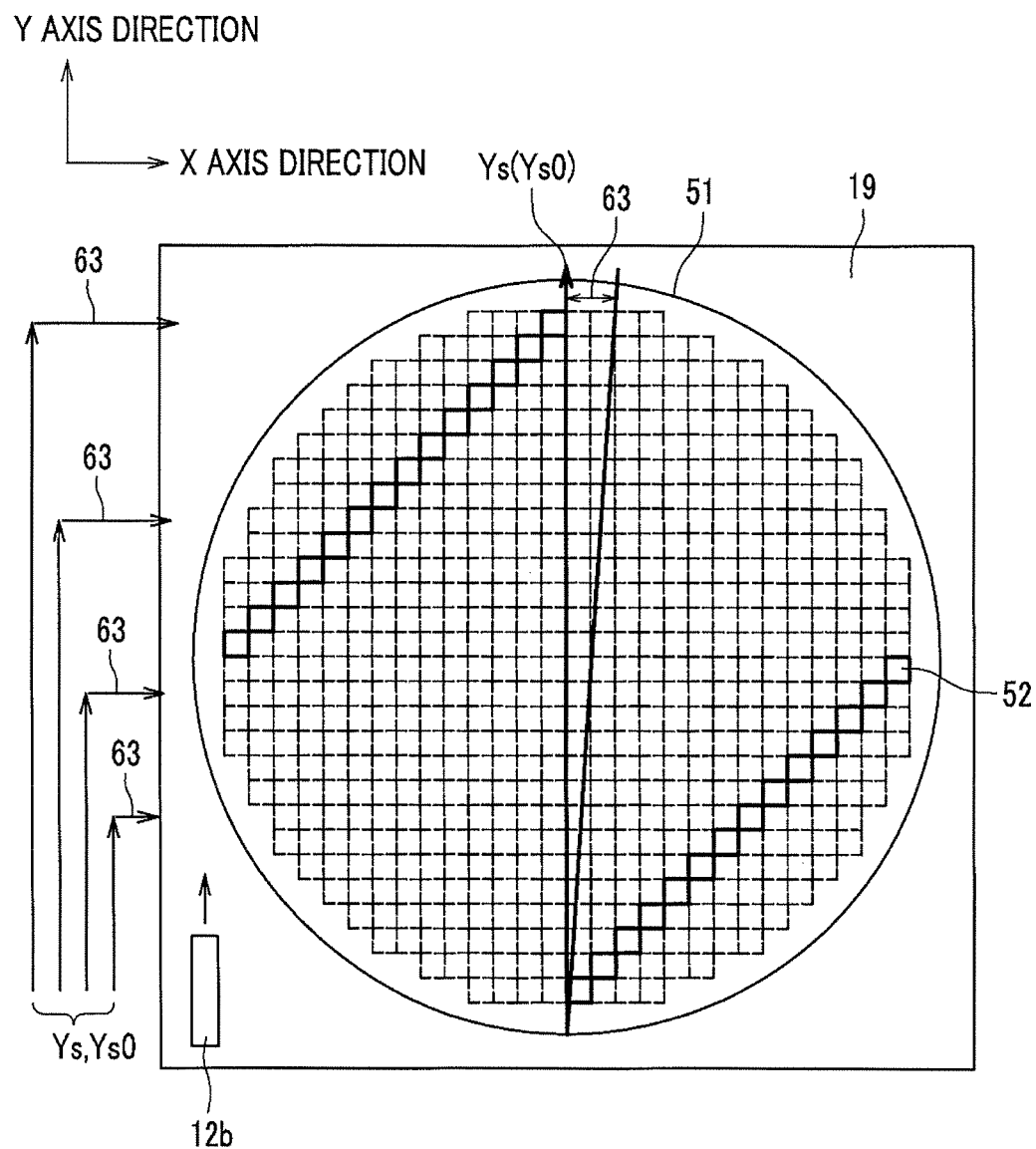
FIG. 13 is a diagram for illustration of errors caused by the orthogonal degree of the stage (orthogonal degree errors)

Using FIG. 13, orthogonal degree errors 63, which are errors along X axis direction generated on a transportation amount along Y axis direction of the stage 19, will be described. A transportation amount along Y axis direction is a relative transportation amount between the line sensor 12b and the stage 19. An orthogonal degree error 63 is generated on a transportation amount (from the coordinate origin) along Y axis direction of the stage 19, namely, a stage Y coordinate Ys (pseudo defect stage Y coordinate Ys0). An orthogonal degree error 63 is generated along X axis direction. The larger the transportation amount (from the coordinate origin) along Y axis direction of the stage 19 (a stage Y coordinate Ys (pseudo defect stage Y coordinate Ys0)), the larger the orthogonal degree error 63. Incidentally, there are not only cases that orthogonal degree errors 63 are generated in a direction from the left to the right along X axis direction, as shown in FIG. 13, but also cases that orthogonal degree errors 63 are generated in an opposite direction from the right to the left.

In the following, coordinate error characteristic patterns will be described. In step S6 in FIG. 2, the characteristic pattern obtaining unit 33 (see FIGS. 1A to 1C) obtains plural, for example, three kinds of coordinate error characteristic patterns. The processing device 21 displays an obtained coordinate error characteristic pattern on the image display device 28. Three kinds of examples of coordinate error characteristic patterns will be taken below.

(1) Shown is a pattern that represents the relationship of a difference ΔX to a pseudo defect stage X coordinate Xs0, and is a coordinate error characteristic pattern CP1 related to inclination error 58 and X scale error 61.

(2) Shown is a pattern that represents the relationship of a difference ΔY to a pseudo defect stage Y coordinate Ys0, and is a coordinate error characteristic pattern CP2 related to magnification ratio error 59 and Y scale 62.

(3) Shown is a pattern that represents the relationship of a difference ΔX to a pseudo defect stage Y coordinate Ys0, and is a coordinate error characteristic pattern CP3 related to inclination error 58 and orthogonal degree error 63.

(1) Coordinate Error Characteristic Pattern CP1

Figure 14:
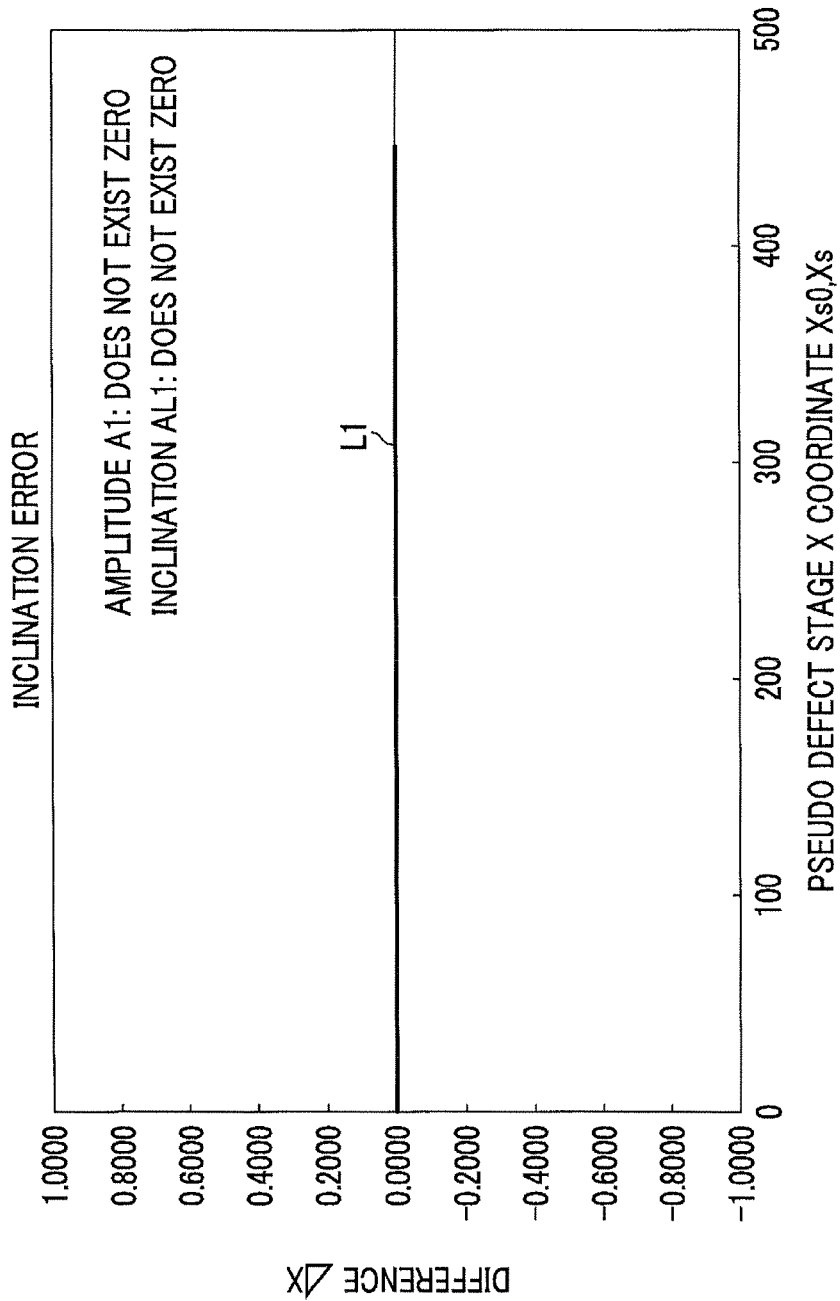
FIG. 14 shows a coordinate error characteristic pattern (No. 1: a case where error (difference) does not exist) representing the relationship of a difference $\Delta X$ from a pseudo defect stage coordinate Xs0.
Figure 15:
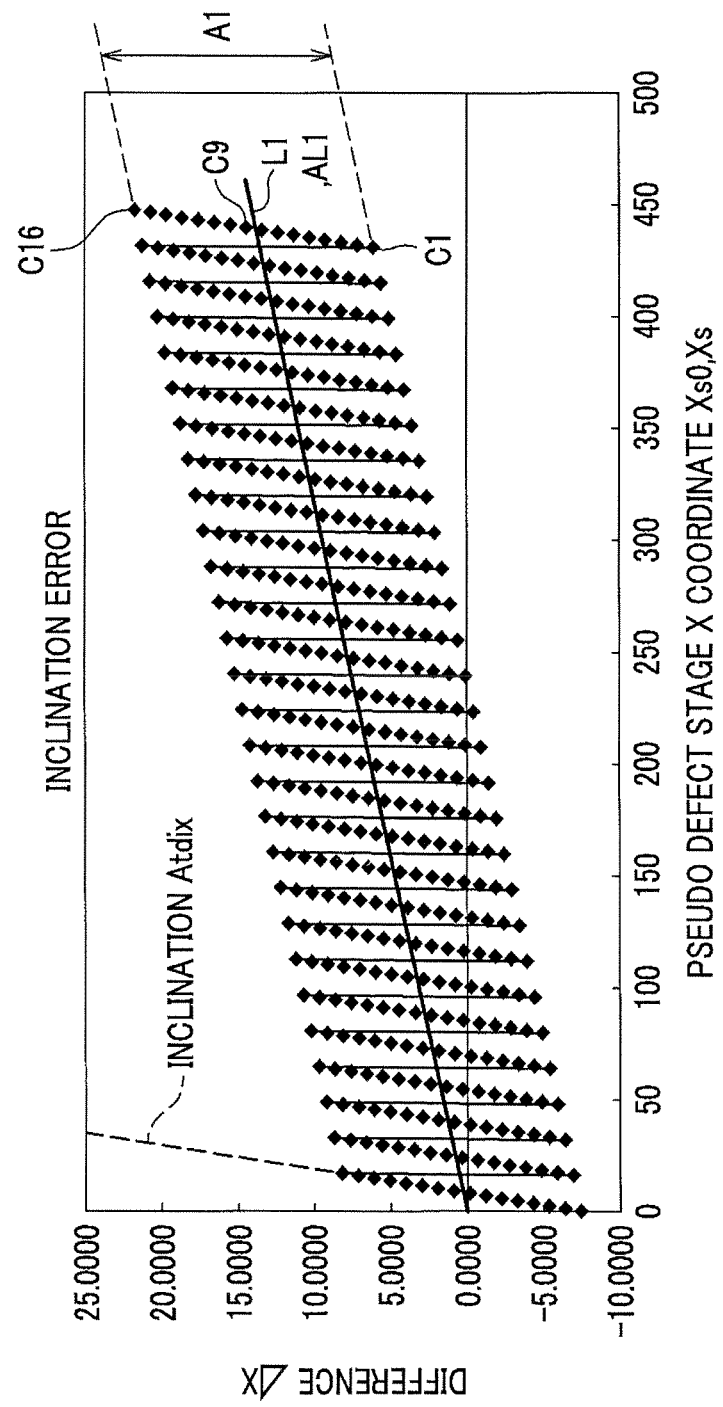
FIG. 15 shows a coordinate error characteristic pattern (No. 2: a case where error (difference) exists) representing the relationship of a difference $\Delta X$ from a pseudo defect stage coordinate Xs0.

FIG. 14 and FIG. 15 show an example of coordinate error characteristic pattern CP1 representing the relationship of a difference ΔX to a pseudo defect stage X coordinate Xs0.

FIG. 14 shows an example of coordinate error characteristic pattern CP1 where neither an inclination error 58 nor an X scale error 61 is generated and difference ΔX does not exist (is zero). In case that neither an inclination error 58 nor an X scale error 61 is generated and difference ΔX does not exist (is zero), as shown in FIG. 14, the coordinate error characteristic pattern CP1 is not dependent on the pseudo defect stage X coordinate Xs0, and becomes a line L1 showing that difference ΔX is zero and constant.

FIG. 15 shows an example of coordinate error characteristic pattern CP1 where inclination error 58 and X scale error 61 are generated and difference ΔX exists (is not zero). In case that inclination errors 58 and X scale errors 61 are generated and difference ΔX exists (is not zero), as shown in FIG. 15, the coordinate error characteristic pattern CP1 is in a sawtooth waveform. The coordinate error characteristic pattern CP1 in this sawtooth waveform vibrates with an amplitude A1 of a sawtooth waveform corresponding to the height of the each sawtooth forming a sawtooth wave. The amplitude A1 is not dependent on the pseudo defect stage X coordinate Xs0 and is constant. Further, the coordinate error characteristic pattern CP1 in the sawtooth waveform tends to increase along the line L1 having an inclination AL1.

The coordinate error characteristic pattern CP1 in the sawtooth waveform is formed by plural sawteeth. The points (black rhombuses in FIG. 15) forming the each sawtooth correspond to the respective channels C1-C9-C16 (12c). In one sawtooth, the difference ΔX by the channel C1 is the smallest, and the difference ΔX by the channel C16 is the largest. Further, in one sawtooth, the pseudo defect stage X coordinate Xs0 by the channel C1 is the smallest, and the pseudo defect stage X coordinate Xs0 by the channel C16 is the largest. Thus, the points (black rhombuses in FIG. 15) forming respective sawteeth are, as shown in FIG. 15, disposed on a line having an inclination Atdix. The amplitude A1 and the inclination Atdix of the sawtooth wave have a correlationship that the larger the amplitude A1 of the sawtooth, the larger the inclination Atdix. It is understood from the above that amplitude A1 and inclination Atdix are caused by inclination error 58. In contrast, it is understood that amplitude A1 and inclination Atdix are not generated by X scale error 61.

On the other hand, the inclination AL1 of the line L1 is dependent on the pseudo defect stage X coordinate Xs0, wherein the larger the pseudo defect stage X coordinate Xs0, the larger the inclination AL1 of the line L1. Accordingly, it is understood that inclination AL1 is generated by X scale error 61. It is also understood that inclination AL1 of line L1 is not generated by inclination error 58.

From the above, inclination error 58 can be detected, based on the amplitude A1 and the inclination Atdix of the coordinate error characteristic pattern CP1, and X scale error 61 can be detected, based on the inclination AL1 of the line L1 of the coordinate error characteristic pattern CP1. According to the coordinate error characteristic pattern CP1, inclination error 58 and X scale error 61 can be detected separately.

Incidentally, FIG. 15 shows an example of a coordinate error characteristic pattern CP1 wherein the inclination AL1 and the inclination Atdix are positive, however, without being limited thereto, the both may be negative. That is, arrangement may be made such that in one sawtooth of a sawtooth waveform of the coordinate error characteristic pattern CP1, the difference ΔX by the channel C1 is the largest while the difference ΔX by the channel C16 is the smallest, and the pseudo defect stage X coordinate Xs0 by the channel C1 is the largest while the pseudo defect stage X coordinate Xs0 by the channel C16 is the smallest. Further, arrangement may be made such that the inclination AL1 of the line L1 is negative, wherein the larger the pseudo defect stage X coordinate Xs0, the smaller the inclination AL1 of the line L1. Further, either the inclination AL1 or the inclination Atdix may be zero. Incidentally, a case that both the inclination AL1 and the inclination Atdix are zero corresponds to the example of a coordinate error characteristic pattern CP1 shown in FIG. 14.

(2) Coordinate Error Characteristic Pattern CP2

Figure 16:
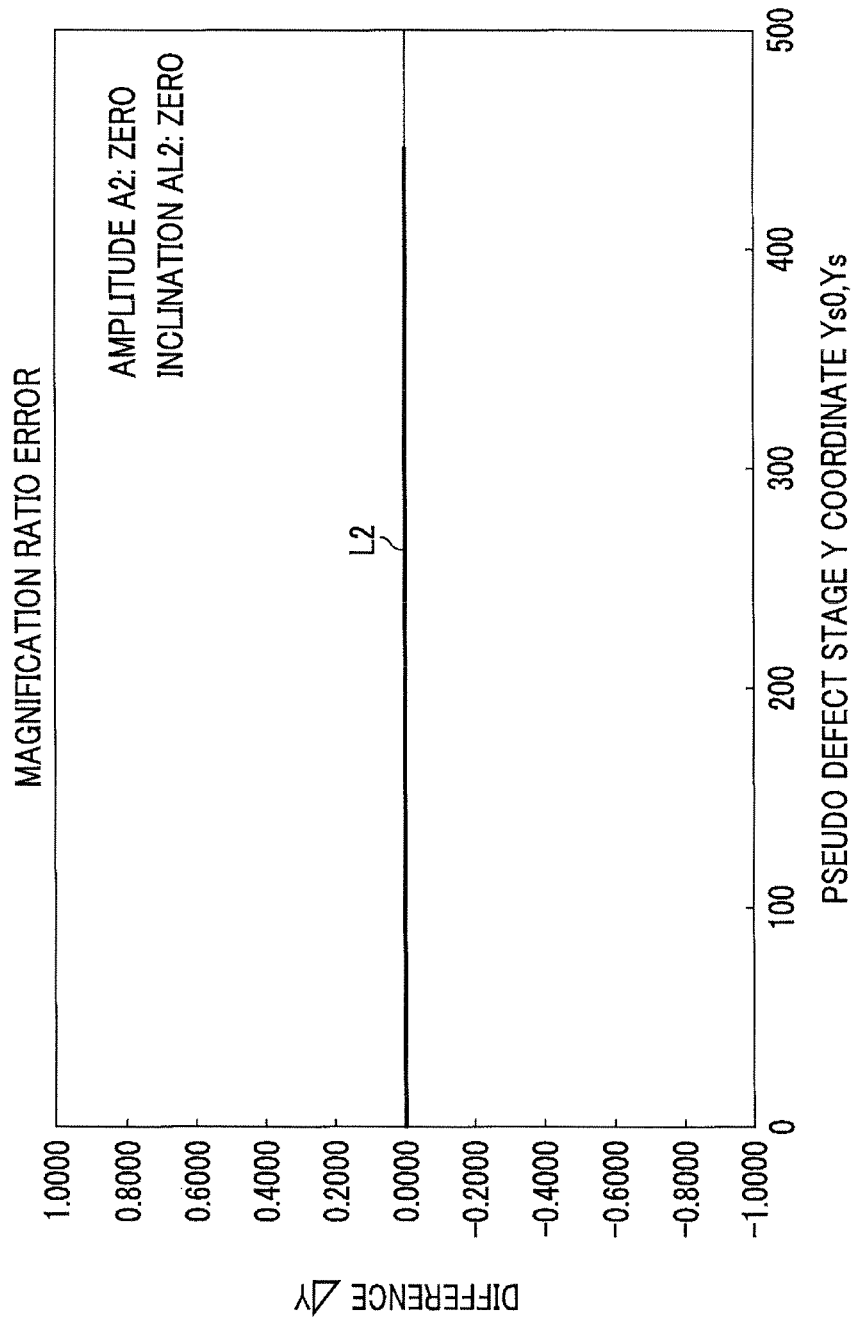
FIG. 16 shows a coordinate error characteristic pattern (No. 1: a case where error (difference) does not exist) representing the relationship of a difference $\Delta Y$ from a pseudo defect stage coordinate Ys0.
Figure 17:
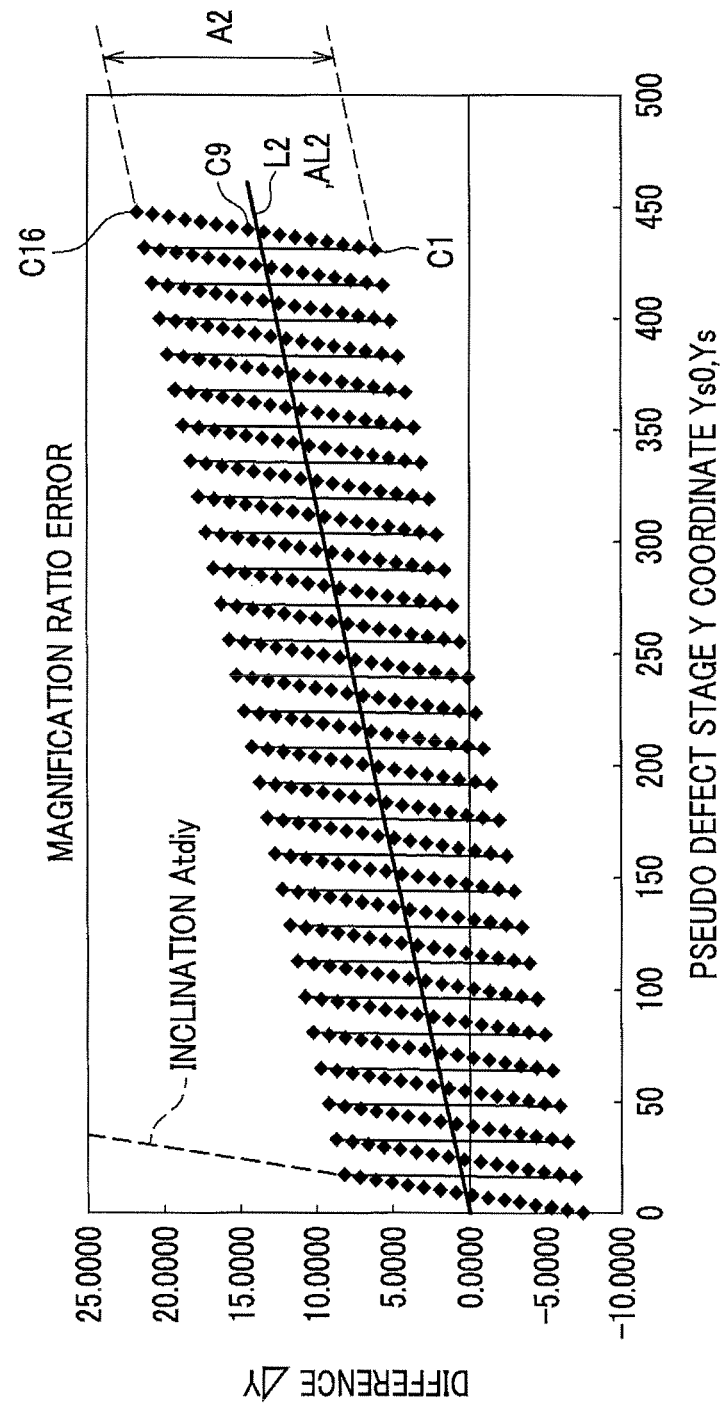
FIG. 17 shows a coordinate error characteristic pattern (No. 2: a case where error (difference) exists) representing the relationship of a difference $\Delta Y$ from a pseudo defect stage coordinate Ys0.

FIG. 16 and FIG. 17 show an example of the coordinate error characteristic pattern CP2 which represents the relationship of difference ΔY to pseudo defect stage Y coordinate Ys0.

FIG. 16 shows an example of coordinate error characteristic pattern CP2 where neither magnification ratio error 59 nor Y scale error 62 is generated and difference ΔY does not exist (is zero). If neither magnification ratio error 59 nor Y scale error 62 is generated and difference ΔY does not exist (is zero), as shown in FIG. 16, the coordinate error characteristic pattern CP2 is not dependent on pseudo defect stage Y coordinate Ys0, and becomes a line L2 showing that the difference ΔY is zero and constant.

FIG. 17 shows an example of coordinate error characteristic pattern CP2 where magnification ratio error 59 and Y scale error 62 are generated and difference ΔY exists (is not zero). In case that magnification ratio error 59 and Y scale error 62 are generated and difference ΔY exists (is not zero), as shown in FIG. 17, the coordinate error characteristic pattern CP2 is in a sawtooth waveform. The coordinate error characteristic pattern CP2 in this sawtooth waveform vibrates with an amplitude A2 of a sawtooth waveform corresponding to the height of the each sawtooth forming a sawtooth wave. The amplitude A2 is not dependent on pseudo defect stage Y coordinate Ys0 and is constant. Further, the coordinate error characteristic pattern CP2 in the sawtooth waveform tends to increase along the line L2 with an inclination AL2.

The coordinate error characteristic pattern CP2 in the sawtooth waveform is formed by plural sawteeth. The points (black rhombuses in FIG. 17) forming respective sawtooth correspond to the respective channels C1-C9-C16 (12c). In one sawtooth, the difference ΔY by the channel C1 is the smallest, and the difference ΔY by the channel C16 is the largest. Further, in one sawtooth, the pseudo defect stage Y coordinate Ys0 by the channel C1 is the smallest, and pseudo defect stage Y coordinate Ys0 by the channel C16 is the largest. Thus, the points (black rhombuses in FIG. 17) forming respective sawteeth are disposed on a line having an inclination Atdiy. The amplitude A2 and the inclination Atdiy of a sawtooth wave have a correlationship that the larger the amplitude A2 of the sawtooth, the larger the inclination Atdiy. It is understood from the above that the amplitude A2 and the inclination Atdiy are caused by a magnification ratio error 59. In contrast, it is understood that neither amplitude A2 nor inclination Atdiy is generated by Y scale error 62.

On the other hand, the inclination AL2 of the line L2 is dependent on pseudo defect stage Y coordinate Ys0, wherein the larger the pseudo defect stage Y coordinate Ys0, the larger the inclination AL2 of the line L2. Accordingly, it is understood that the inclination AL2 is generated by Y scale error 62. It is also understood that the inclination AL2 of the line L2 is not generated by magnification ratio error 59.

From the above, magnification ratio error 59 can be detected, based on the amplitude A2 and the inclination Atdiy of the coordinate error characteristic pattern CP2, and Y scale error 62 can be detected, based on the inclination AL2 of the line L2 of the coordinate error characteristic pattern CP2. According to the coordinate error characteristic pattern CP2, magnification ratio error 59 and Y scale error 62 can be detected separately.

Incidentally, as an example of coordinate error characteristic pattern CP2, FIG. 17 shows such that the inclination AL2 and the inclination Atdiy are positive, however, without being limited thereto, both of these may be negative. That is, arrangement may be made such that in one sawtooth of a sawtooth waveform of the coordinate error characteristic pattern CP2, the difference ΔY by the channel C1 is the largest while the difference ΔY by the channel C16 is the smallest, and the pseudo defect stage Y coordinate Ys0 by the channel C1 is the largest while the pseudo defect stage Y coordinate Ys0 by the channel C16 is the smallest. Further, arrangement may be made such that the inclination AL2 of the line L2 is negative, wherein the larger the pseudo defect stage Y coordinate Ys0, the smaller the inclination AL2 of the line L2. Further, either the inclination AL2 or the inclination Atdiy may be zero. Incidentally, a case that both the inclination AL2 and the inclination Atdiy are zero corresponds to the example of a coordinate error characteristic pattern CP2 shown in FIG. 16.

(3) Coordinate Error Characteristic Pattern CP3

Figure 18:
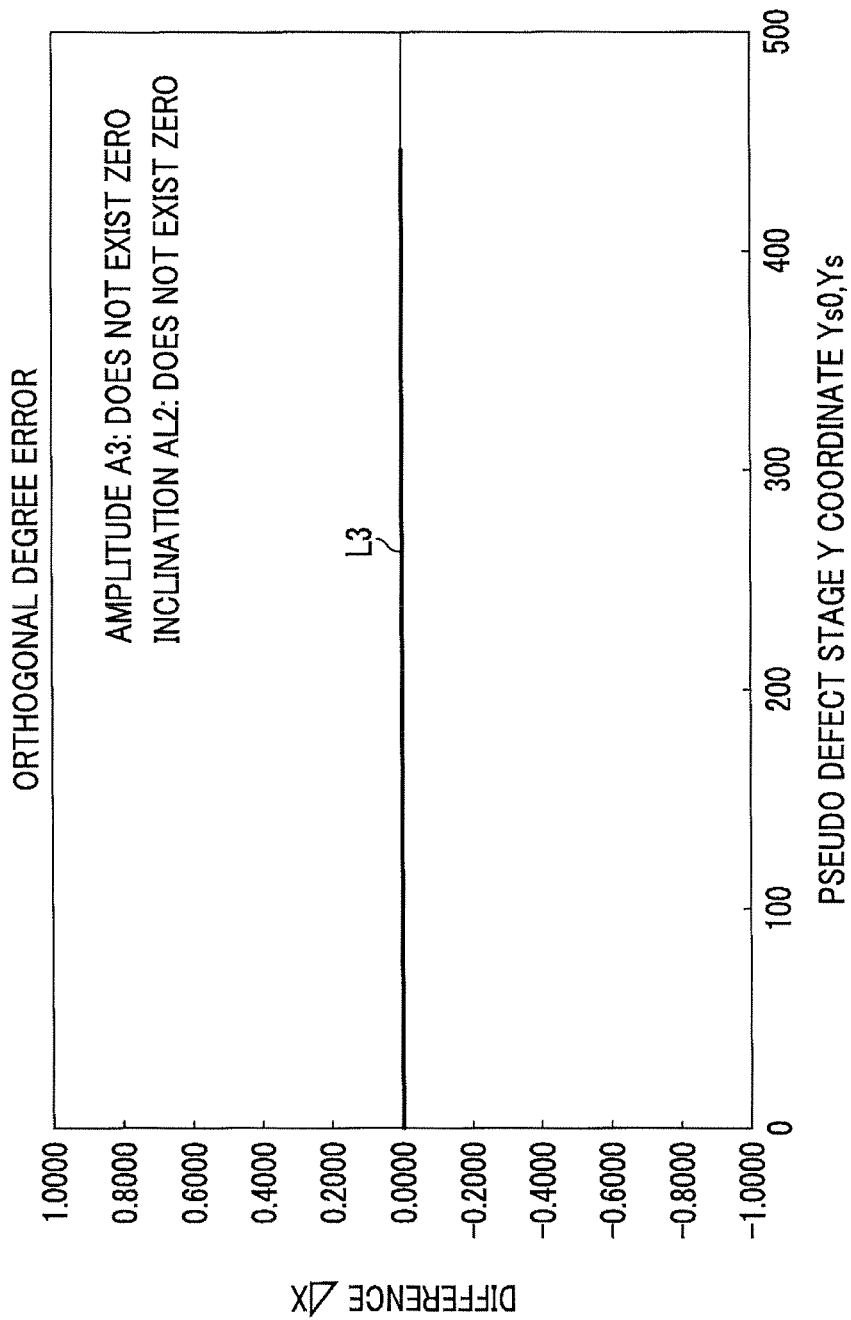
FIG. 18 shows a coordinate error characteristic pattern (No. 1: a case where error (difference) does not exist) representing the relationship of a difference $\Delta X$ from a pseudo defect stage coordinate Ys0.
Figure 19:
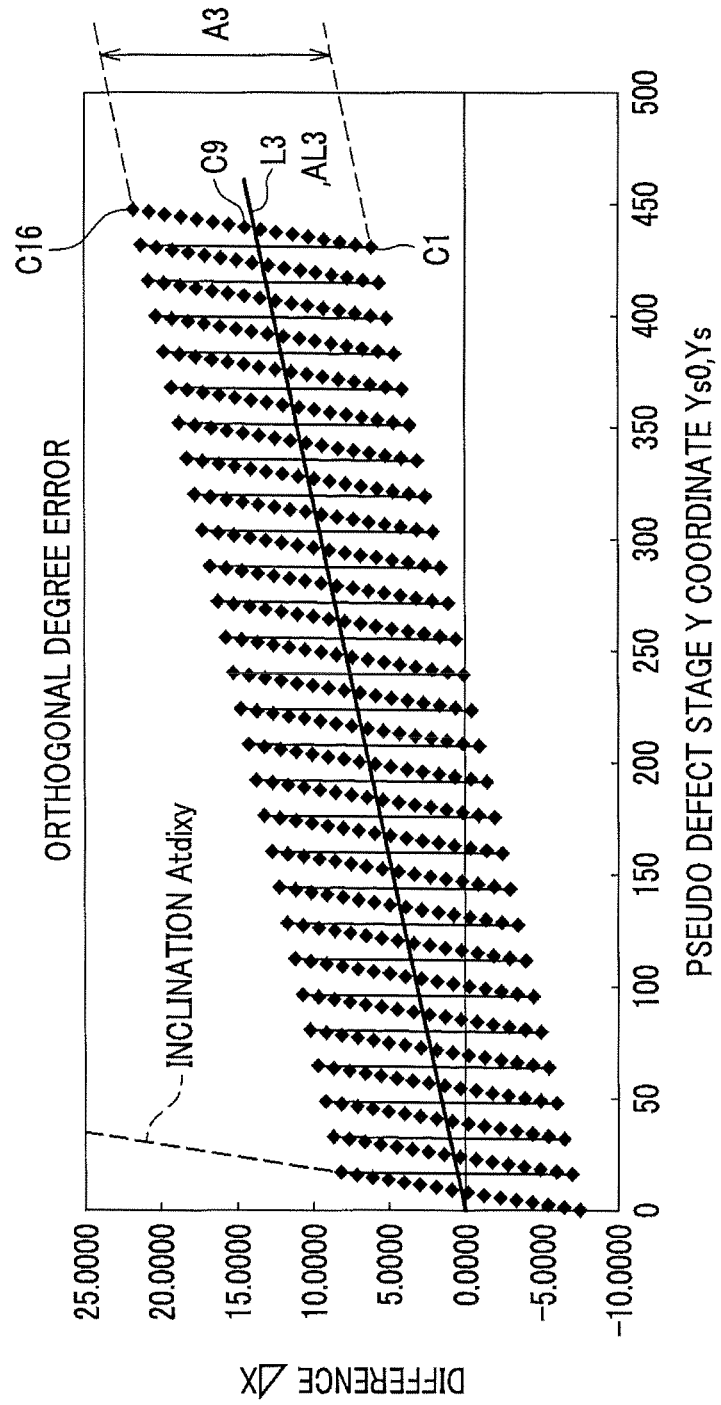
FIG. 19 shows a coordinate error characteristic pattern (No. 2: a case where error (difference) exists) representing the relationship of a difference $\Delta X$ from a pseudo defect stage coordinate Ys0.

FIG. 18 and FIG. 19 show an example of the coordinate error characteristic pattern CP3 which represents the relationship of difference ΔX to pseudo defect stage Y coordinate Ys0.

FIG. 18 shows an example of coordinate error characteristic pattern CP3 where neither inclination error 58 nor orthogonal degree error 63 is generated and difference ΔX does not exist (is zero). In case that neither inclination error 58 nor orthogonal degree error 63 is generated and difference ΔX does not exist (is zero), as shown in FIG. 18, the coordinate error characteristic pattern CP3 is not dependent on pseudo defect stage Y coordinate Ys0, and becomes a line L3 which shows that the difference ΔX is zero and constant.

FIG. 19 shows an example of coordinate error characteristic pattern CP3 where inclination error 58 and orthogonal degree error 63 are generated and difference ΔX exists (is not zero). In case that inclination error 58 and orthogonal degree error 63 are generated and difference ΔX exists (is not zero), as shown in FIG. 19, the coordinate error characteristic pattern CP3 is in a sawtooth waveform. The coordinate error characteristic pattern CP3 in this sawtooth waveform vibrates with an amplitude A3 of a sawtooth waveform corresponding to the height of the each sawtooth forming a sawtooth wave. The amplitude A3 is not dependent on pseudo defect stage Y coordinate Ys0 and is constant. Further, the coordinate error characteristic pattern CP3 in the sawtooth waveform tends to increase along the line L3 with an inclination AL3.

The coordinate error characteristic pattern CP3 in the sawtooth waveform is formed by plural sawteeth. The points (black rhombuses in FIG. 19) forming respective sawteeth correspond to the respective channels C1-C9-C16 (12c). In one sawtooth, the difference ΔX by the channel C1 is the smallest, and the difference ΔX by the channel C16 is the largest. Further, in one sawtooth, the pseudo defect stage Y coordinate Ys0 by the channel C1 is the smallest, and the pseudo defect stage Y coordinate Ys0 by the channel C16 is the largest. Thus, the points (black rhombuses in FIG. 19) forming respective sawteeth are disposed on a line having an inclination Atdixy. The amplitude A3 and the inclination Atdixy of the sawtooth wave have a correlationship that the larger the amplitude A3 of the sawtooth, the larger the inclination Atdixy. It is understood from the above that the amplitude A3 and the inclination Atdixy are caused by inclination error 58. In contrast, it is understood that amplitude A3 and the inclination Atdixy are not generated by orthogonal degree error 63.

On the other hand, the inclination AL3 of the line L3 is dependent on pseudo defect stage Y coordinate Ys0, wherein the larger the pseudo defect stage Y coordinate Ys0, the larger the inclination AL3 of the line L3. Accordingly, it is understood that the inclination AL3 is generated by orthogonal degree error 63. It is also understood that the inclination AL3 of the line L3 is not generated by inclination error 58.

From the above, the inclination error 58 can be detected, based on the amplitude A3 and the inclination Atdixy of the coordinate error characteristic pattern CP3, and orthogonal degree error 63 can be detected, based on the inclination AL3 of the line L3 of the coordinate error characteristic pattern CP3. According to the coordinate error characteristic pattern CP3, inclination error 58 and the orthogonal degree error 63 can be detected separately.

Incidentally, as an example of coordinate error characteristic pattern CP3, FIG. 19 shows such that the inclination AL3 and the inclination Atdixy are positive, however, without being limited thereto, both of these may be negative. That is, arrangement may be made such that in one sawtooth of a sawtooth waveform of the coordinate error characteristic pattern CP3, the difference ΔX by the channel C1 is the largest while the difference ΔX by the channel C16 is the smallest, and the pseudo defect stage Y coordinate Ys0 by the channel C1 is the largest while the pseudo defect stage Y coordinate Ys0 by the channel C16 is the smallest. Further, arrangement may be made such that the inclination AL3 of the line L3 is negative, wherein the larger the pseudo defect stage Y coordinate Ys0, the smaller the inclination AL3 of the line L3. Further, either the inclination AL3 or the inclination Atdixy may be zero. Incidentally, a case that both the inclination AL3 and the inclination Atdixy are zero corresponds to the example of a coordinate error characteristic pattern CP3 shown in FIG. 18.

Returning to FIG. 2, in step S7, the processing device 21 displays the coordinate error characteristic patterns CP1, CP2, and CP3 to the operator, and prompts determination whether or not the coordinate error characteristic patterns CP1, CP2, and CP3 are appropriate via GUI. If coordinate error characteristic patterns CP1, CP2, and CP3, such as shown in FIGS. 14 to 19 are displayed, the operator determines appropriateness (step S7, Yes), and the process proceeds to step S8, and if a display is made otherwise (step S7, No), the operator determines inappropriateness, and the process proceeds to step S4.

In step S8, the inclination obtaining unit 34 determines the lines L1, L2, and L3 having the inclinations AL1, AL2, and AL3, based on the coordinate error characteristic patterns CP1, CP2, and CP3. Further, the amplitude obtaining unit 35 determines the lines having the inclinations Atdix, Atdiy, and Atdixy, based on the coordinate error characteristic patterns CP1, CP2, and CP3. The amplitude obtaining unit 35 determines the upper and the lower end of sawteeth used in computing the amplitudes A1, A2, and A3, based on the coordinate error characteristic patterns CP1, CP2, and CP3.

Further, in step S8, the stage correction factor computing unit 36 computes the inclinations AL1, AL2, and AL3 as stage correction factors, based on the determined lines L1, L2, and L3. The inclinations AL1, AL2, and AL3, which are stage correction factors, represent ratios of errors generated on the transportation of the stage 19.

Concretely, the inclination AL1, which is a stage correction factor, represents the ratio of generated X scale error 61 (difference ΔX) to stage X coordinate Xs of the stage 19. Accordingly, by multiplying the stage X coordinate Xs by the inclination AL1, which is the stage correction factor, the X scale error 61 (difference ΔX) at the stage X coordinate Xs can be computed.

Concretely, the inclination AL2, which is a stage correction factor, represents the ratio of generated Y scale error 62 (difference ΔY) to stage Y coordinate Ys of the stage 19. Accordingly, by multiplying the stage Y coordinate Ys by the inclination AL2, which is the stage correction factor, the Y scale error 62 (difference ΔY) at the stage Y coordinate Ys can be computed.

Concretely, the inclination AL3, which is a stage correction factor, represents the ratio of generated orthogonal degree error 63 (difference ΔX) to stage Y coordinate Ys of the stage 19. Accordingly, by multiplying the stage Y coordinate Ys by the inclination AL3, which is the stage correction factor, the orthogonal degree error 63 (difference ΔX) at the stage Y coordinate Ys can be computed.

Further, in step S8, the channel correction factor computing unit 37 computes the amplitudes A1, A2, and A3, based on the determined upper and the lower end of sawteeth. Then, based on the amplitudes A1, A2, and A3, the channel correction factor computing unit 37 computes channel correction factors, which are the ratios of errors to the pitch Pc of the channels 12c, the errors being due to the channels 12c. Concretely, the channel correction factor computing unit 37 computes the inclinations Atdix, Atdiy, and Atdixy as channel correction factors, based on the lines having the determined inclinations Atdix, Atdiy, and Atdixy.

The inclination Atdix, which is a channel correction factor, represents the ratio of inclination error 58 (difference ΔX) to the pitch Pc of channels 12c (the pitch Pd of pseudo defects 54), the inclination error 58 being due to the channel 12c. As an inclination error 58 is generated for each pseudo defect die 52, the inclination error 58 (difference ΔX) at a die X coordinate Xd can be computed by multiplying the die X coordinate Xd by the inclination Atdix, which is the channel correction factor.

The inclination Atdiy, which is a channel correction factor, represents the ratio of the magnification ratio error 59 (difference ΔY) to the pitch Pc of channels 12c (the pitch Pd of pseudo defects 54), the inclination error 58 being due to the channel 12c. As a magnification ratio error 59 is generated for each pseudo defect die 52, the magnification ratio error 59 (difference ΔY) at a die Y coordinate Yd can be computed by multiplying the die Y coordinate Yd by the inclination Atdiy, which is the channel correction factor.

The inclination Atdixy, which is a channel correction factor, represents the ratio of the inclination error 58 (difference ΔX) to the pitch Pc of channels 12c (the pitch Pd of pseudo defects 54), the inclination error 58 being due to the channel 12c. As an inclination error 58 is generated for each pseudo defect die 52, the inclination error 58 (difference ΔX) at a die Y coordinate Yd can be computed by multiplying the die Y coordinate Yd by the inclination Atdixy, which is the channel correction factor.

In step S9 in FIG. 2, the storing/transmitting unit 41 stores the inclinations AL1, AL2, AL3, which are stage correction factors, and the inclinations Atdix, Atdiy, and Atdixy, which are channel correction factors.

Then, in step S10, the optical type inspection apparatus 1 again performs inspection of the entire surface of the wafer for coordinates management 51, using the scan table created in step S2. However, differently from the inspection of the entire surface in step S4, in the inspection of the entire surface of this time in step S10, the correction factors, which have become zero by initialization, are changed to the inclination AL1, AL2, or AL3, which are stage correction factors, and the inclination Atdix, Atdiy, or Atdixy, which are channel correction factors.

Then, first, similarly to step S4, all the pseudo defects 54 in the wafer for coordinates management 51 and the pseudo defect dies 52 are detected, and pseudo defect stage coordinates (pseudo X coordinate Xs0, pseudo defect stage Y coordinate Ys0), which are at the positions where these have been detected, are detected by the stage position detecting units (Y scale, X scale, and coordinate management device) 13, 14, and 25 (see FIGS. 1A to 1C). The coordinate transforming unit 31 (see FIGS. 1A to 1C) transforms the detected pseudo defect stage coordinates (pseudo defect stage X coordinate Xs0, pseudo defect stage Y coordinate Ys0) into pseudo defect die coordinates (pseudo defect die X coordinate Xd0, pseudo defect die Y coordinate Yd0), which represent the potions in the pseudo defect dies 52 including the corresponding pseudo defects 54. The storing/transmitting unit 41 (see FIGS. 1A to 1C) stores the pseudo defect stage coordinates (pseudo defect stage X coordinate Xs0, pseudo defect stage Y coordinate Ys0) and the pseudo defect die coordinates (pseudo defect die X coordinate Xd0, pseudo defect die Y coordinate Yd0).

That is, in step S10, differently from step S4, further, the pseudo defect die coordinates (pseudo defect die X coordinate Xd0, pseudo defect die Y coordinate Yd0) are corrected for high accuracy. Concretely, the stage correction amount computing unit 38 multiply the pseudo defect coordinates (pseudo defect stage X coordinate Xs0, pseudo defect stage Y coordinate Ys0) having been detected in this step S10 by a stage correction factor, and thereby computes stage correction amounts.

More concretely, as represented by Expression (1), by multiplying a pseudo defect stage X coordinate Xs0 by an inclination AL1 which is a stage correction factor, the X scale error 61 (difference ΔX) at the pseudo defect stage X coordinate Xs0, namely, the stage correction amount ΔXds (No. 1) can be computed.

$$\Delta Xds(X \text{ scale error } 61) = Xs0 \times AL1 \tag{1}$$

Likewise, as represented by Expression (2), by multiplying a pseudo defect stage Y coordinate Ys0 by an inclination AL2, which is a stage correction factor, the Y scale error 62 (difference ΔY) at the pseudo defect stage Y coordinate Ys0, namely, the stage correction amount ΔYds can be computed.

$$\Delta Yds(Y \text{ scale error } 62) = Ys0 \times AL2 \tag{2}$$

As represented by Expression (3), by multiplying a pseudo defect stage Y coordinate Ys0 by an inclination AL3, which is a stage correction factor, the orthogonal degree error 63 (difference ΔX) at the pseudo defect stage Y coordinate Ys0, namely, the stage correction amount ΔXds (No. 2) can be computed.

$$\Delta Xds(\text{orthogonal degree error } 63) = Ys0 \times AL3 \tag{3}$$

The computation of these stage correction amounts means performing back calculation of computation of the stage correction factors in step S8, and means performing so-called proof calculation. The correctness of this proof calculation is verified in steps S10 to S13.

Concretely, the die correction amount computing unit 39 computes die correction amounts by multiplying the pseudo defect die coordinates (pseudo defect die X coordinate Xd0, pseudo defect die Y coordinate Yd0) by channel correction factors.

More concretely, as represented by Expression (4), by multiplying a pseudo defect die X coordinate Xd0 by an inclination Atdix, which is a channel correction factor, the inclination error 58 (difference ΔX) at the pseudo defect die X coordinate Xd0, namely, the die correction amount ΔXdd (No. 1) can be computed.

$$\Delta Xdd(\text{inclination error 58}) = Xd0 \times Atdix \quad (4)$$

Likewise, as represented by Expression (5), by multiplying a pseudo defect die Y coordinate Yd0 by an inclination Atdiy, which is a channel correction factor, the magnification ratio error 59 (difference ΔY) at the pseudo defect die Y coordinate Yd0, namely, the die correction amount ΔYdd can be computed.

$$\Delta Ydd(\text{magnification ratio error 59}) = Yd0 \times Atdiy \quad (5)$$

As represented by Expression (6), by multiplying a pseudo defect die Y coordinate Yd0 by an inclination Atdixy, which is a channel correction factor, the inclination error 58 (difference ΔX) at the pseudo defect die Y coordinate Yd0, namely, the die correction amount ΔXdd (No. 2) can be computed. Incidentally, both a die correction amount ΔXdd (No. 1) and a correction amount ΔXdd (No. 2) correspond to an inclination error 58, wherein it is only necessary to compute either one.

$$\Delta Xdd(\text{inclination error 58}) = Yd0 \times Atdixy \quad (6)$$

The computation of these die correction amounts means performing back calculation of computation of the channel correction factors in step S8, and means performing so-called proof calculation. The correctness of this proof calculation is verified in steps S10 to S13.

A pseudo defect stage coordinate (pseudo defect stage X coordinate Xs0, pseudo defect stage Y coordinate Ys0) and a pseudo defect die coordinate (pseudo defect die X coordinate Xd0, pseudo defect die Y coordinate Yd0) are different in coordinate system, however, the both represent the same one point (the position of the same pseudo defect 54) on the wafer for coordinates management 51 (pseudo defect die 52). The correction amount at this one point can be computed as the sum of the stage correction amount and the die correction amount.

That is, as represented by Expression (7), the die coordinate correcting unit 40 adds a stage correction amount ΔXds (X scale error 61), a stage correction amount ΔXds (orthogonal degree error 63), and a die correction amount ΔXdd (inclination error 58) to a pseudo defect die X coordinate Xd0 (or a pseudo defect stage X coordinate Xs0), and thereby computes a corrected pseudo defect die X coordinate Xdm0 (or a corrected pseudo defect stage X coordinate Xsm0).

$$Xdm0(Xsm0) = Xd0(Xs0) + \Delta Xds(X \text{ scale error 61}) + \\ \Delta Xds(\text{orthogonal degree error 63}) + \Delta Xdd(\text{inclination error 58}) \quad (7)$$

Further, as represented by Expression (8), the die coordinate correcting unit 40 adds a stage correction amount ΔYds (Y scale error 62) and a die correction amount ΔYdd (magnification ratio error 59) to a pseudo defect die Y coordinate Yd0 (or a pseudo defect stage Y coordinate Ys0), and thereby computes a corrected pseudo defect die Y coordinate Ydm0 (or a corrected pseudo defect stage Y coordinate Ysm0).

$$Ydm0(Ysm0) = Yd0(Ys0) + \Delta Yds(Y \text{ scale error 62}) + \\ \Delta Ydd(\text{magnification ratio error 59}) \quad (8)$$

The storing/transmitting unit 41 (see FIGS. 1A to 1C) stores corrected pseudo defect die X coordinates Xdm0 (or corrected pseudo defect stage X coordinates Xsm0) and corrected pseudo defect die Y coordinates Ydm0 (or corrected pseudo defect stage Y coordinates Ysm0). Now, step S10 is completed. Incidentally, although inspection of the entire surface of the wafer for coordinates management 51 is performed also in step S4, as the correction factors (the stage correction factors AL1, AL2, and AL3, and the channel correction factors Atdix, Atdiy, and Atdixy) are set to zero (AL1 AL2, AL3, Atdix, Atdiy, Atdixy =0), the stage correction amounts ΔXds (X scale errors 61) are zero (ΔXds (X scale errors 61) =0), according to Expression (1); the stage correction amounts ΔYds (Y scale error 62) are zero (ΔYds (Y scale errors 62) =0), according to Expression (2); the stage correction amounts ΔXds (orthogonal degree error 63)are zero (ΔXds (orthogonal degree errors 63) =0), according to Expression (3); the die correction amounts ΔXdd (inclination error 58) are zero (ΔXdd (inclination errors 58) =0), according to Expression (4); the die correction amounts ΔYdd (magnification ratio errors 59) are zero (die correction amounts ΔYdd (magnification ratio error 59) =0),according to Expression (5); and the die correction amounts ΔXdd (inclination errors 58) are zero (ΔXdd (inclination errors 58) =0), according to Expression (6). By these, in Expression (7), the corrected pseudo defect die X coordinates Xdm0 (or the corrected pseudo defect stage X coordinates Xsm0) become equal to the pseudo defect die X coordinates Xd0 (or the pseudo defect stage X coordinates Xs0), in other words (Xdm0(Xsm0) =Xd0(Xs0); and in Expression (8), the corrected pseudo defect die Y coordinates Ydm0 (or the corrected pseudo defect stage Y coordinates Ysm0) become equal to the pseudo defect die Y coordinates Yd0 (or the pseudo defect stage Y coordinates Ys0), in other words, Ydm0 (Ysm0) =Yd0(Ys0). In such a manner, the pseudo defect die X coordinates Xd0 (or the pseudo defect stage X coordinates Xs0) and the pseudo defect die Y coordinates Yd0 (or the pseudo defect stage Y coordinates Ys0) are virtually obtained.

Then, in step S11 similarly to the process in step S5, the difference computing unit 32 computes differences ΔX (=Xdm0−Xd2), ΔY (=Ydm0−Yd2) of the corrected pseudo defect die coordinates (corrected pseudo defect die X coordinate Xdm0, corrected pseudo defect die Y coordinate Ydm0) from designed coordinates (designed X coordinate Xd2, designed Y coordinate Yd2) which are based on design, wherein the differences ΔX and ΔY are generated when the pseudo defects 54 are formed in the pseudo defect dies 52.

Then, in step S12 similarly to the process in step S6, the characteristic pattern obtaining unit 33 obtains coordinate error characteristic patterns CP1, CP2, and CP3, using the computed differences ΔX and ΔY computed in step S11, and displays them on the image display device 28. Further, for comparison, the characteristic pattern obtaining unit 33 also displays the coordinate error characteristic patterns CP1, CP2, and CP3 obtained in step S6 on the image display device 28.

In step S13, the processing device 21 displays for the operator the coordinate error characteristic patterns CP1, CP2, and CP3 having been obtained in step S12 and step S6 via GUI, and prompts the operator to determine whether or not errors are eliminated by correction (whether correction is appropriate) from the characteristic patterns CP1, CP2, and CP3 obtained in step S12. If errors, as shown in FIG. 14, FIG. 16, and FIG. 18, are eliminated and coordinate error characteristic patterns CP1, CP2, and CP3 are displayed as if errors were not generated, the operator determines that the correction is appropriate (step S13, Yes) and the process proceeds to step S14. On the other, if display is made not in such a manner, the operator determines that the correction is not appropriate (step S13, No), and the process returns to step S4. Incidentally, if the correction is appropriate, the differences ΔX and ΔY computed in step S11 result in zero. Herein, determination whether or not the correction is appropriate may be determined, dependent on whether or not the differences ΔX and AY computed in step S11 are within a predetermined value near zero, as shown in step S13 in FIG. 2.

If the step proceeds to step S14, it is understood that accurate correction of the defect coordinates can be made with the obtained correction factors. Steps S14 and after will be described on a case of inspecting a mass production wafer.

In step S14, the optical type inspection apparatus 1 performs inspection of the entire surface of a mass production wafer 71, using a scan table for a mass production wafer 71, the scan table having been prepared in advance. Similarly to the entire surface inspection in step S10, in the entire surface inspection of this time in step S14, correction factors are set to the inclinations AL1, AL2, and AL3, which are the stage correction factors computed in step S8, and the inclinations Atdix, Atdiy, and Atdixy, which are the channel correction factors computed in step S8.

Figure 20:
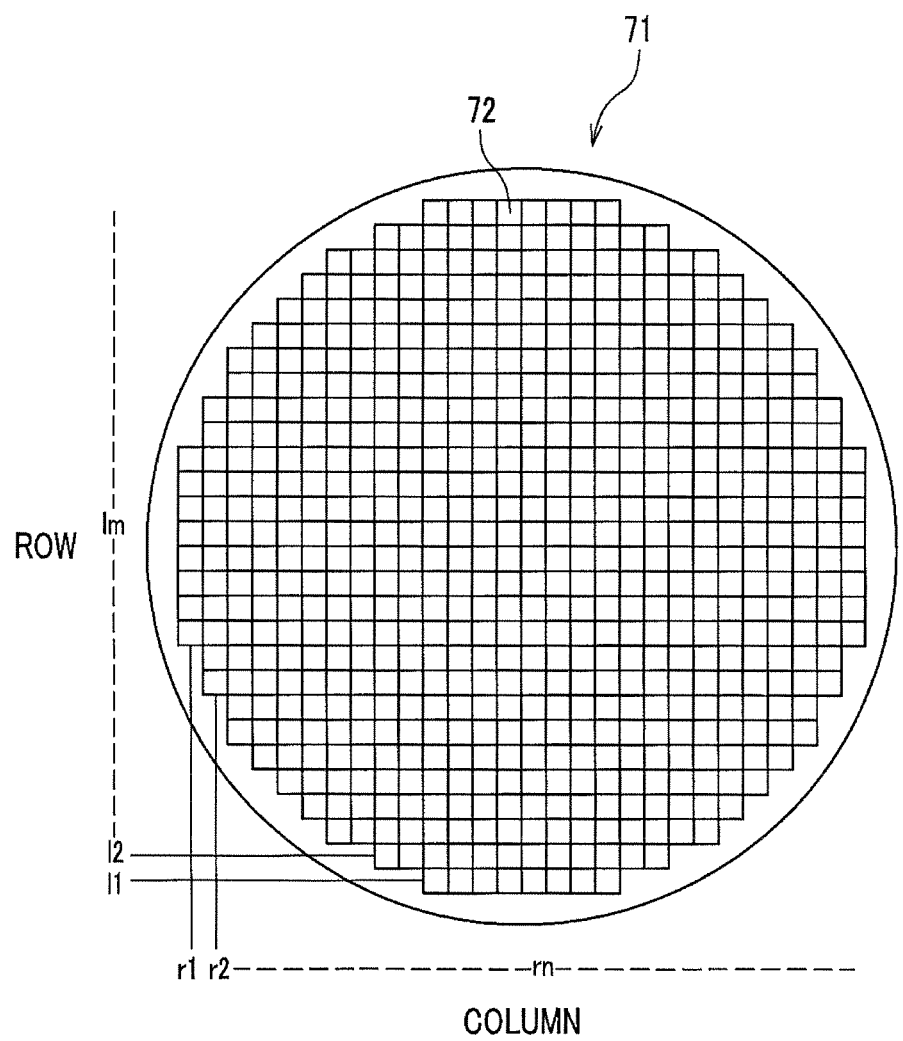
FIG. 20 is a plan view of a mass production wafer.

FIG. 20 shows a plan view of the mass production wafer 71 under manufacturing. A matrix is set on the surface of the mass production wafer 71. Plural rows l1, l2, . . . , lm, . . . and plural columns r1, r2, . . . rn, . . . are set in the matrix. Mass production dies 72 are formed on all the columns r1, r2, rn, . . . across the respective rows l1, l2, . . . , lm, . . . .

Figure 21:
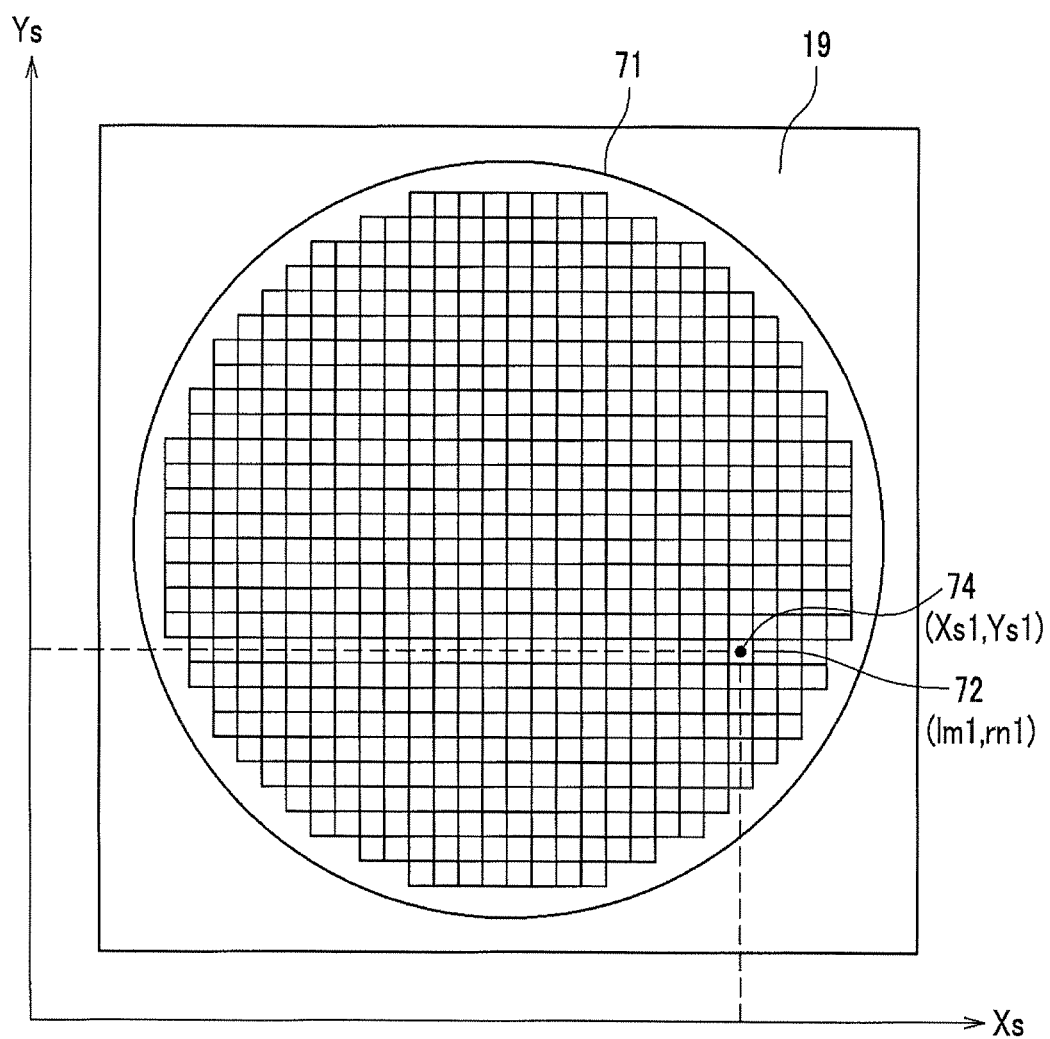
FIG. 21 is a diagram for illustration of the relationship between a stage coordinate and a real defect stage coordinate on a mass production wafer, and shows a mass production wafer fixed on a stage.

FIG. 21 shows the mass production wafer 71, which is fixed on the stage 19. The mass production wafer 71 is provided with mass production dies 72. As shown in FIG. 21, for example, it will be assumed that a real defect 74 is generated in the mass production die 72 at the row/column (lm1, rn1). As described later, the real defect 74 is determined to be a defect by the defect determination device 24 in FIGS. 1A to 1C, and a real defect stage coordinate (a real defect stage Y coordinate Ys1 and a real defect stage X coordinate Xs1) is stored in the inspection result storage device 26, as the position where the real defect 74 is located on stage coordinate (a stage Y coordinate Ys and a stage X coordinate Xs).

Figure 22:
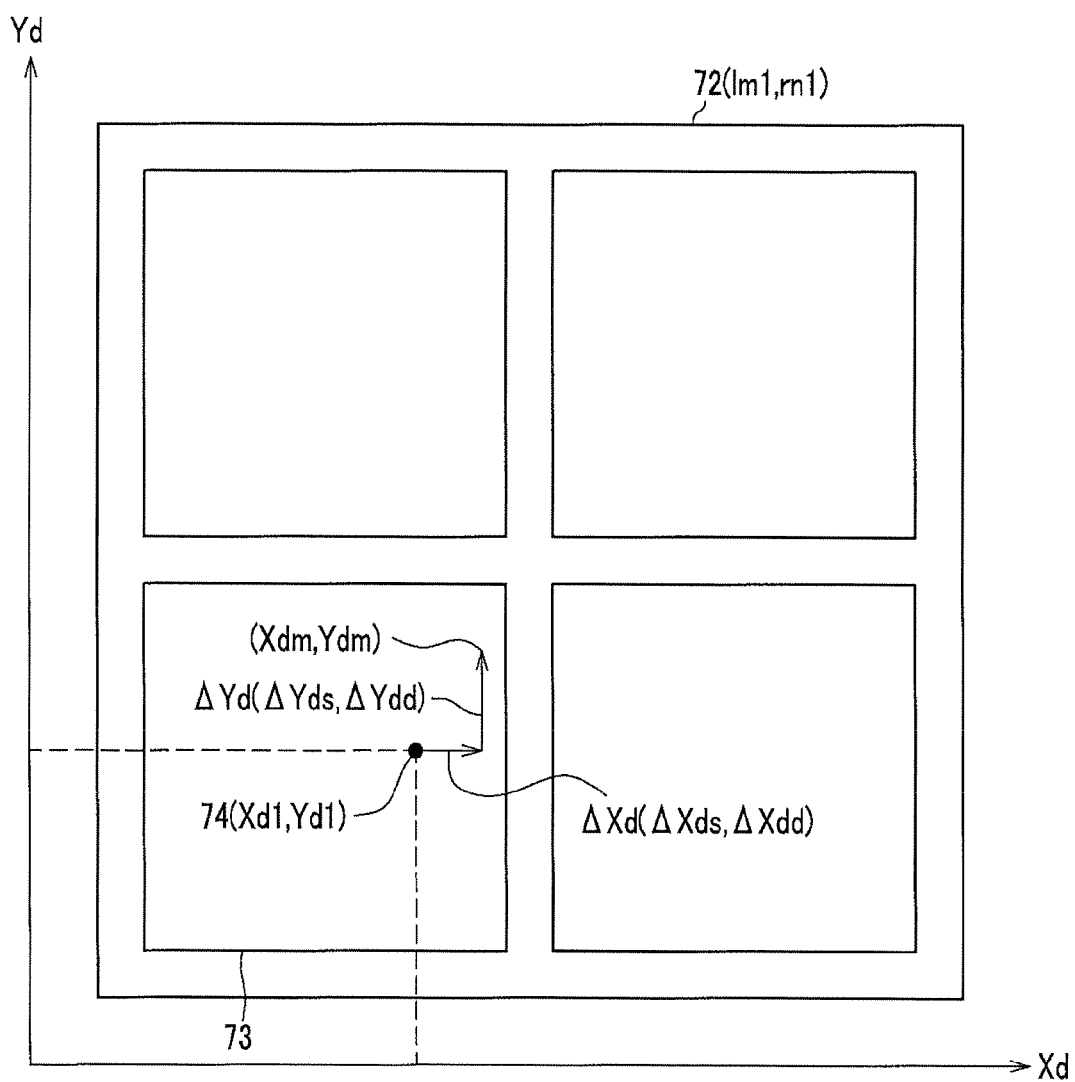
FIG. 22 is a diagram for illustration of the relationship between a die coordinate and a real defect die coordinate on a mass production die formed on a mass production wafer, and shows a plan view of a mass production die.

FIG. 22 shows a plan view of mass production dies 72. Die cells 73 are formed in the mass production dies 72. In the example in FIG. 22, totally four die cells 73 are formed on vertically and horizontally 2 rows. It is assumed that a real defect 74 is generated in one die cell 73 out of the four die cells 73. The real defect 74 shown in FIG. 22 is the same as the real defect 74 shown in FIG. 21 and is generated at the same position, however, the coordinate systems representing the position are different between FIG. 21 and FIG. 22. In FIG. 21, the position of the real defect 74 is expressed as a real defect stage coordinate (real defect stage Y coordinate Ys1 and real defect stage X coordinate Xs1), by the use of stage coordinate (stage Y coordinate Ys and stage X coordinate Xs). On the other hand, in FIG. 22, the position of the real defect 74 is expressed as a real defect die coordinate (real defect die Y coordinate Yd1 and real defect die X coordinate Xd1), by the use of die coordinate (die Y coordinate Yd and die X coordinate Xd). The real defect stage coordinate (real defect stage Y coordinate Ys1 and real defect stage X coordinate Xs1) can be transferred with one to one relationship into real defect die coordinate (real defect die Y coordinate Yd1 and real defect die X coordinate Xd1).

In the entire surface inspection of the mass production wafer 71, if correction factors (stage correction factors AL1, AL2, AL3, channel correction factors Atdix, Atdiy, Atdixy), which are not zero, are set in advance, it is considered that a real defect stage coordinate (real defect stage Y coordinate Ys1 and real defect stage X coordinate Xs1) or a real defect die coordinate (real defect die Y coordinate Yd1 and real defect die X coordinate Xd1) includes errors 58-63, and correction is accordingly performed. In the correction, a correction amount ΔXd (ΔXds, ΔXdd) is added to the real defect die X coordinate Xd1 to compute a corrected real defect die X coordinate Xdm, and a correction amount AYd (ΔYds, ΔYdd) is added to the real defect die Y coordinate Yd1 to compute a corrected real defect die Y coordinate Ydm. Thus, a highly accurate defect coordinate (corrected real defect die X coordinate Xdm, corrected real defect die Y coordinate Ydm) can be obtained.

That is, in step S14, the following is performed. All real defects 74 in the mass production wafer 71 and the mass production dies 72 are detected, and real defect stage coordinates (real defect stage X coordinate Xs1, real defect stage Y coordinate Ys1), which are the positions where the real defects 74 have been detected, are detected by the stage position detecting units (Y scale, X scale, coordinate management device) 13, 14, and 25 (see FIGS. 1A to 1C). The coordinate transforming unit 31 (see FIGS. 1A to 1C) transforms the detected real defect stage coordinates (real defect stage X coordinate Xs1, real defect stage Y coordinate Ys1) into real defect die coordinates (real defect die X coordinate Xd1, real defect die Y coordinate Yd1) representing the positions in the mass production dies 72 where the corresponding real defects 74 are included. The storing/transmitting unit 41 (see FIGS. 1A to 1C) stores the real defect stage coordinates (real defect stage X coordinate Xs1, real defect stage Y coordinate Ys1) and the real defect die coordinates (real defect die X coordinate Xd1, real defect die Y coordinate Yd1).

Further, in step S14 in FIG. 2, the stage correction amount computing unit 38 multiplies the real defect stage coordinates (real defect stage X coordinate Xs1, real defect stage Y coordinate Ys1), which have been detected in this step S14, by stage correction factors, and thereby computes stage correction amounts.

Concretely, as expressed by Expression (11), the stage correction amount computing unit 38 multiplies a real defect stage X coordinate Xs1 by the inclination AL1, which is a stage correction factor, and thereby computes an X scale error 61 (difference ΔX), namely a stage correction amount ΔXds (No. 1), at the real defect stage X coordinate Xs1.

$$\Delta Xds(X \text{ scale error } 61) = Xs1 \times AL1 \tag{11}$$

Likewise, as expressed by Expression (12), the stage correction amount computing unit 38 multiplies a real defect stage Y coordinate Ys1 by the inclination AL2, which is a stage correction factor, and thereby computes a Y scale error 62 (difference ΔY), namely a stage correction amount ΔYds, at the real defect stage Y coordinate Ys1.

$$\Delta Yds(Y \text{ scale error } 62) = Ys1 \times AL2 \tag{12}$$

As expressed by Expression (13), the stage correction amount computing unit 38 multiplies the real defect stage Y coordinate Ys1 by the inclination AL3, which is a stage correction factor, and thereby computes an orthogonal degree error 63 (difference ΔX), namely a stage correction amount ΔXds (No, 2), at the real defect stage Y coordinate Ys1.

$$\Delta Xds(\text{orthogonal degree error 63}) = Ys1 \times AL3 \quad (13)$$

Further, in step S14 in FIG. 2, the die correction amount computing unit 39 computes a die correction amount by multiplying the real defect die coordinate (real defect die X coordinate Xd1, real defect die Y coordinate Yd1) by a channel correction factor.

Concretely, as represented by Expression (14), by multiplying the real defect die X coordinate Xd1 by the inclination Atdix, which is a channel correction factor, the die correction amount computing unit 39 computes the inclination error 58 (difference ΔX), namely the die correction amount ΔXdd (No. 1), at the real defect die X coordinate Xd1.

$$\Delta Xdd(\text{inclination error 58}) = Xd1 \times Atdix \quad (14)$$

Likewise, as represented by Expression (15), by multiplying the real defect die Y coordinate Yd1 by the inclination Atdiy, which is a channel correction factor, the die correction amount computing unit 39 computes a magnification ratio error 59 (difference ΔY), namely the die correction amount ΔYdd, at the real defect die Y coordinate Yd1.

$$\Delta Ydd(\text{magnification ratio error 59}) = Yd1 \times Atdiy \quad (15)$$

As represented by Expression (16), by multiplying the real defect die Y coordinate Yd1 by the inclination Atdixy, which is a channel correction factor, the die correction amount computing unit 39 computes an inclination error 58 (difference ΔX), namely the die correction amount ΔXdd (No. 2), at the real defect die Y coordinate Yd1. Incidentally, both the die correction amount ΔXdd (No. 1) and the die correction amount ΔXdd (No. 2) correspond to the inclination error 58, wherein it is only necessary to compute either one.

$$\Delta Xdd(\text{inclination error 58}) = Yd1 \times Atdixy \quad (16)$$

A real defect stage coordinate (real defect stage X coordinate Xs1, real defect stage Y coordinate Ys1) and a real defect die coordinate (real defect die X coordinate Xd1, real defect die Y coordinate Yd1) are different in the coordinate system, however, the both represent the same one point (the position of the same real defect 74) on the mass production wafer 71 (mass production die 72). The correction amount at this one point can be computed as the sum of the stage correction amount and the die correction amount.

That is, as represented by Expression (17), the die coordinate correcting unit 40 adds a stage correction amount ΔXds (X scale error 61), a stage correction amount ΔXds (orthogonal degree error 63), and a die correction amount ΔXdd (inclination error 58) to the real defect die X coordinate Xd1 (or the real defect stage X coordinate Xs1), and thereby computes a corrected real defect die X coordinate Xdm (or a corrected real defect stage X coordinate Xsm) (corrected defect coordinate).

$$Xdm(Xsm) = Xd1(Xs1) + \Delta Xds(X \text{ scale error } 61) + \quad (17)$$
$$\Delta Xds(\text{orthogonal degree error } 63) + \Delta Xdd(\text{inclination error } 58)$$

Further, as represented by Expression (18), the die coordinate correcting unit 40 adds a stage correction amount ΔYds (Y scale error 62) and a die correction amount ΔYdd (magnification ratio error 59) to the real defect die Y coordinate Yd1 (or the real defect stage Y coordinate Ys1), and thereby computes a corrected real defect die Y coordinate Ydm (or a corrected real defect stage Y coordinate Ysm) (corrected defect coordinate).

$$Ydm(Ysm) = Yd1(Ys1) + \Delta Yds(Y \text{ scale error } 62) + \quad (18)$$
$$\Delta Ydd(\text{magnification ratio error } 59)$$

The storing/transmitting unit 41 stores corrected real defect die X coordinates Xdm (or corrected real defect stage X coordinates Xsm) and corrected real defect die Y coordinates Ydm (or corrected real defect stage Y coordinates Ysm). Now, step S14 is completed.

In step S15 in FIG. 2, the storing/transmitting unit 41 transmits, to the review device, the corrected real defect die X coordinates Xdm (or the corrected real defect stage X coordinates Xsm) and the corrected real defect die Y coordinates Ydm (or the corrected real defect stage Y coordinates Ysm), which are corrected defect coordinates. As the review device can obtain corrected defect coordinates with high accuracy, it is possible to surely display a real defect 74, even displaying the peripheral region of the correction defect coordinates with high magnification ratio. Now, the flow of the method of correcting defect coordinate, shown in FIG. 2, can be completed.

Figure 23:
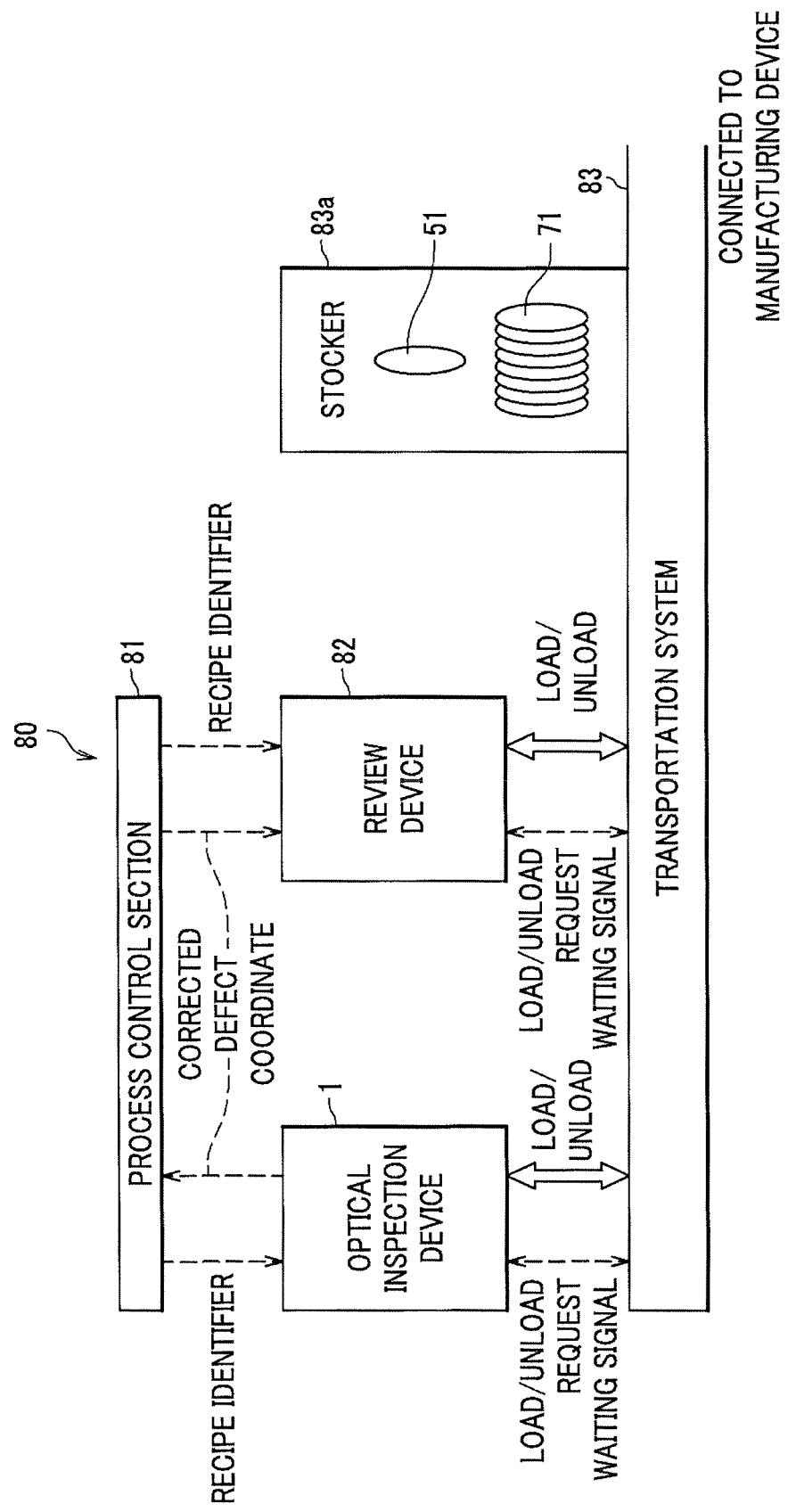
FIG. 23 is a configuration diagram of an inspection system in the embodiment according to the present invention.

FIG. 23 shows a configuration diagram of an inspection system 80 in the present embodiment according to the present invention. The inspection system 80 is provided with the optical type inspection apparatus 1 in the present embodiment according to the present invention. Further, the inspection system 80 includes a process control section 81, a review device 82, and a transportation system 83.

The optical type inspection apparatus 1 and the review device 82 store recipes used in performing entire surface inspection of a wafer for coordinates management 51 or a mass production wafer 71, displaying defects with magnification, or the like. These recipes may include a scan table. Each recipe is associated with a recipe identifier, and a recipe to be used for entire surface inspection can be read out, based on a recipe identifier received from the process control section 81.

The process control section 81 transmits, to the optical type inspection apparatus 1 and the review device 82, a recipe identifier corresponding to a wafer, such as a wafer for coordinates management 51 or a mass production wafer 71 to be loaded. Thus, the process control section 81 can manage the manufacturing process of mass production wafers 71 and manage the accuracy of defect coordinate on the optical type inspection apparatus 1.

The review device 82 receives corrected defect coordinates (Xdm, Ydm) obtained by the optical type inspection apparatus 1, directly or via the process control section 81. The review device 82 displays, with magnification, the periphery of a position represented by a corrected defect coordinate (Xdm, Ydm) on the mass production wafer 71, and can thereby display, with magnification, a real defect 74 at the corrected defect coordinate (Xdm, Ydm). The manufacturer of mass production wafers 71 used for a semiconductor device or a display device observes real defects 74 displayed with magnification, and can thereby find the generation cause of real defects 74 or reduce real defects 74.

The transportation system 83 includes a stocker 83a capable of reserving a wafer for coordinates management 51 or a mass production wafer 71. The transportation system 83 is connected with the optical type inspection apparatus 1 and the review device 82, so as to load and unload a wafer for coordinates management 51 or a mass production wafer 71. Further, the transportation system 83 is also connected with a manufacturing device for processing mass production wafers 71, so as to load and unload a mass production wafer 71.

When a mass production wafer 71, for which a process by the manufacturing device has once completed, is ready to be processed by the optical type inspection apparatus 1, the transportation system 83 once reserves the mass production wafer 71 by the stocker 83a, and transmits an inspection waiting signal to the optical type inspection apparatus 1 to notify the optical type inspection apparatus 1 of the fact that there is wafer waiting for a process (inspection). After receiving the inspection waiting signal, when the optical type inspection apparatus 1 has become ready to perform entire surface inspection, the optical type inspection apparatus 1 transmits a load requesting signal to the transportation system 83 to request for loading the mass production wafer 71. After receiving the load requesting signal, the transportation system 83 loads the mass production wafer 71 onto the optical type inspection apparatus 1. Based on a recipe identifier obtained from the process control section 81, the optical type inspection apparatus 1 reads out a recipe (scan table), and based on the recipe, performs entire surface inspection of the mass production wafer 71. Thus, (data of) corrected defect coordinates are created. After completing the entire surface inspection, the optical type inspection apparatus 1 transmits an unload requesting signal to the transportation system 83 to request for unloading the mass production wafer 71. Further, the optical type inspection apparatus 1 transmits (the data of) the corrected defect coordinates to the process control section 81. The process control section 81 once stores (the data of) the corrected defect coordinates. After receiving the unload requesting signal, the transportation system 83 unloads the mass production wafer 71 from the optical type inspection apparatus 1, then once reserves the mass production wafer 71 by the stocker 83a, and transmits a waiting signal to the review device 82 to notify the fact that there is a wafer waiting for processing.

After receiving the waiting signal, when the review device 82 has become ready to perform displaying of real defects 74 with magnification, the review device 82 transmits a load requesting signal to the transportation system 83 to request for loading the mass production wafer 71. After receiving the load requesting signal, the transportation system 83 loads the mass production wafer 71 onto the review device 82. The review device 82 receives a recipe identifier and the corrected defect coordinates from the process control section 81. Based on the recipe identifier, the review device 82 reads out a recipe (scan table), and based on the recipe, displays with magnification a real defect 74 at a corrected defect coordinates on the mass production wafer 71. After completing the process of displaying with magnification the real defects 74, the review device 82 transmits an unload requesting signal to the transportation system 83 to request for unloading the mass production wafer 71. After receiving the unload requesting signal, the transportation system 83 unloads the mass production wafer 71 from the review device 82, then once reserves the mass production wafer 71 by the stocker 83a, and transmits a waiting signal to the manufacturing device to notify the fact that there is a wafer waiting for processing.

Figure 24:
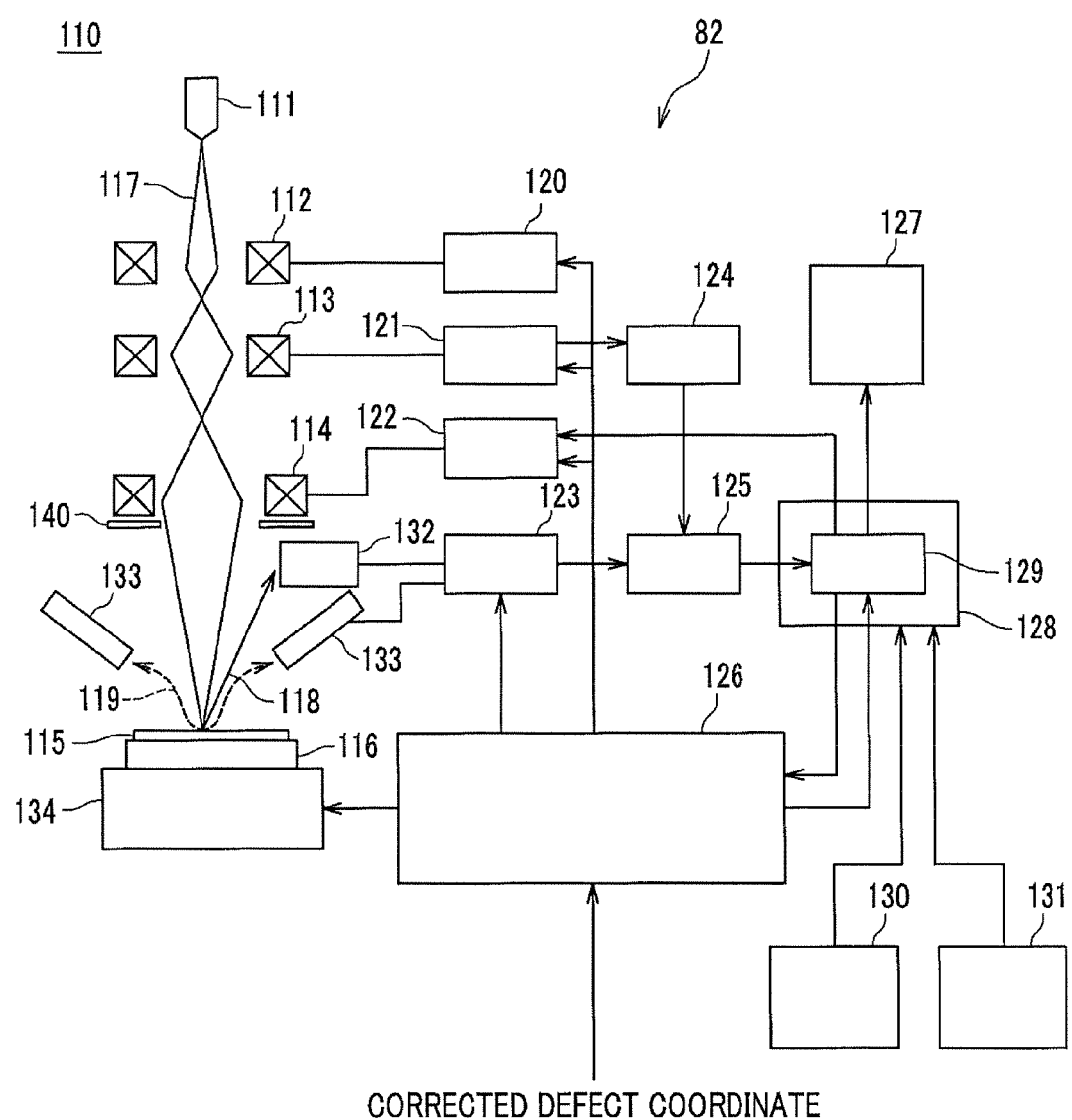
FIG. 24 is a configuration diagram of a review device used for the inspection system in the embodiment according to the present invention.

FIG. 24 shows a configuration diagram of the review device 82. An electron scanning microscope is applied to the review device 82. The vacuum container of an electron optical column 110 is not shown. An electron beam 117 generated by an electron gun 111 is projected through a condenser lens 112, a deflector 113, and an objective lens 114 to a mass production wafer (specimen) 115. The electron beam 117 is narrowed by the condenser lens 112 and the objective lens 114, and deflected by the deflector 113 so as to scan the surface of the mass production wafer 115 in order to obtain images with certain dimensions wherein a corrected defect coordinate is disposed at the center of an image. The excitation intensity of the condenser lens 112 is controlled by a condenser lens control unit 120. The deflection amount by the deflector 113 is controlled by a deflector control unit 121 so as to obtain the images with the certain dimensions wherein a corrected defect coordinate is disposed at the center of an image. The excitation intensity of the objective lens 114 is controlled by an objective lens control unit 122. The control amounts of the above-described controls are computed by a processor 129 of a computer 128 and transmitted from a control unit 126 to respective control units.

When the electron beam 117 is projected to the mass production wafer 115, secondary signals, such as secondary electrons and reflected electrons having information of the shape and the material of the mass production wafer 115 (real defect 74), are generated. Secondary signals generally include secondary electrons 118 with an energy lower than 50 eV and reflected electrons 119 with a higher energy. The secondary electrons 118 are detected by a lifting force and an upper detector 132, not shown, and reflected electrons 119 are detected by plural detectors 133. By a detector control unit 123, detected secondary signals 118, 119 are amplified, converted from an analog signal into a digital signal, and stored in an image memory 125 as image data. The plural detectors 133 are installed in such a manner, for example, that two detectors 133 face each other in order to obtain three dimensional information. The two detectors 133 are controlled by the detector control unit 123. For a real defect 74 of the mass production wafer 115, the detector control unit 123 generates an L image from a reflected electron (signal) 119 on the left side, and an R image from a reflected electron (signal) 119 on the right side. On the other hand, the detector control unit 123 generates an S image of a secondary electron image from a secondary electron 118 detected by the detector 132.

An address control unit 124 generates an address, which is synchronized with a scan signal of an electron beam 117, from deflection control data transmitted from the deflector control unit 121 such that a corrected defect coordinate is disposed at the center of an image, and the address is stored in the image memory 125, being associated with an image signal from the detector control unit 123. The image memory 125 transmits the stored image data (L image, R image, S image) to the computer 128. From the image data, the computer 128 performs computation of a later-described evaluation value for focusing, fitting of the evaluation value by a function, and computation of the peak of the fitting function, generates a focus adjusting signal, and transmits the focus adjusting signal to the objective lens control unit 122. The objective lens control unit 122 controls the excitation intensity of the objective lens 114 to adjust the focal point. For adjusting the focal point, there is a method of adjusting a focal point, using an input tool 130 or a dedicated input tool 131, while the operator is viewing an image displayed on a display 127, and there is also a method of automatic focusing that automatically adjust a focal point, based on the evaluation value of an obtained image, while the objective lens control unit 122 is changing the focal point of the objective lens 114. The input tool 130 is an ordinary keyboard or a mouse, and the dedicated input tool 131 is a dedicated input tool provided with a joystick or a trackball for adjusting the electron scanning microscope. As another method of adjusting a focal point, as described in Japanese Patent Application Laid-Open No. 2007-242605, the position of a focal point may be changed by providing an electrostatic electrode, not shown, in the magnetic path of the objective lens 114 and changing an applied voltage to this electrostatic electrode. The mass production wafer 115 is fixed by a specimen table 116, such as an electrostatic chuck, and can be transported on a two dimensional plane in X axis direction and Y axis direction by a transporting stage 134 moved by a control signal from the control unit 126. A function to transport, as necessary, the mass production wafer 115 along Z axis direction, which is the height direction, may be provided.

Figure 25:
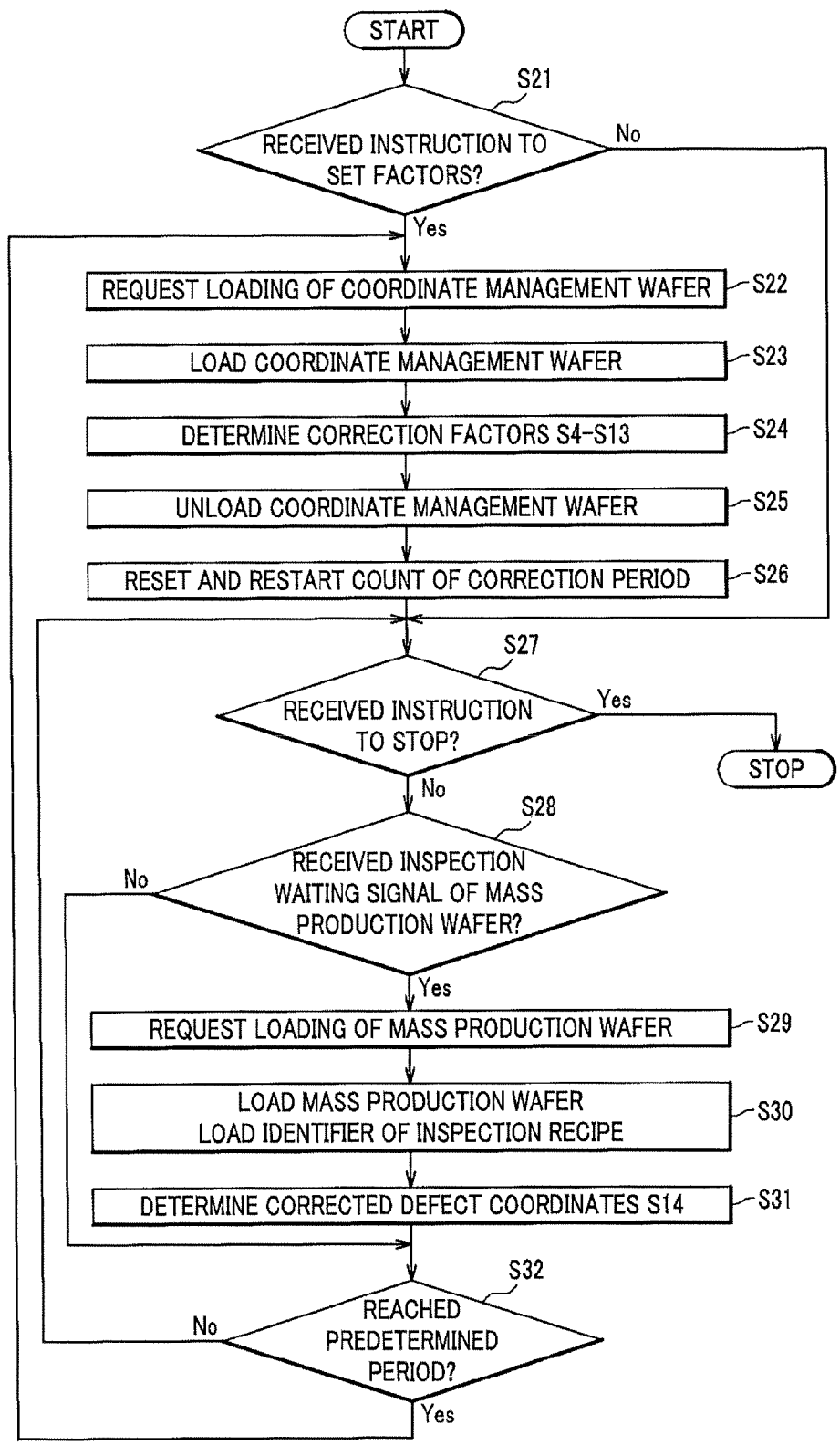
FIG. 25 is a flowchart of an operation method (a method of correcting defect coordinates) of the inspection system in the embodiment according to the present invention.

FIG. 25 is a flowchart of an operation method (a method of correcting defect coordinates) of the inspection system 80.

First, in step S21, the processing device 21 of the optical type inspection apparatus 1 determines whether or not an instruction to set (reset) correction factors has been input to the processing device 21 by the operator. If an instruction to set (reset) correction factors has been input (step S21, Yes), the process proceeds to step S22, and if an instruction to set (reset) correction factors has not been input (step S21, No), the process proceeds to step S27.

Then, in step S22, the processing device 21 of the optical type inspection apparatus 1 transmits a request to the transportation system 83 to load a wafer for coordinates management 51.

In step S23, the transportation system 83 loads a wafer for coordinates management 51 reserved in the stocker 83a onto the optical type inspection apparatus 1.

In step S24, the processing device 21 of the optical type inspection apparatus 1 determines correction factors (AL1, AL2, and AL3, which are stage correction factors, and inclinations Atdix, Atdiy, and Atdixy, which are channel correction factors). Concretely, steps S1 to S13 in FIG. 2 are executed. Incidentally, once steps S1 to S3 in FIG. 2 are executed at the first time, steps S1 to S3 can be omitted from the second time as a wafer for coordinates management 51 and a scan table prepared at the first time can be used. Accordingly, steps S4 to S13 are executed from the second time.

In step S25, the processing device 21 of the optical type inspection apparatus 1 transmits a request to the transportation system 83 to unload the wafer for coordinates management 51. The transportation system 83 unloads the wafer for coordinates management 51 from the optical type inspection apparatus 1 onto the stocker 83a.

In step S26, the processing device 21 of the optical type inspection apparatus 1 resets the timer 42 (see FIGS. 1A to 1C) that counts the correction period, and restarts the timer 42.

In step S27, the processing device 21 of the optical type inspection apparatus 1 determines whether or not an instruction to stop the process has been input to the processing device 21 by the operator. If a strop instruction has been input (step S27, Yes), the processing device 21 stops the flow of the operation method (method of correcting defect coordinates) of the inspection system 80, and if a stop instruction has not been input (step S27, No), the process proceeds to step S28.

In step S28, the processing device 21 of the optical type inspection apparatus 1 determines whether or not an inspection waiting signal has been received from the transportation system 83, wherein the inspection waiting signal notifies that there is a mass production wafer 71 waiting for processing (inspection). If an inspection waiting signal has been received (step S28, Yes), the process proceeds to step S29, and if an inspection waiting signal has not been received (step S28, No), the process proceeds to step S32.

In step S29, the processing device 21 of the optical type inspection apparatus 1 transmits a load request to the transportation system 83 to load the mass production wafer 71 waiting for processing (inspection).

In step S30, the transportation system 83 loads the mass production wafer 71 waiting for processing (inspection) onto the optical type inspection apparatus 1. Further, the process control section 81 loads an identifier of an inspection recipe to the processing device 21 of the optical type inspection apparatus 1.

In step S31, the processing device 21 of the optical type inspection apparatus 1 detects real defects 74 of the mass production wafer 71, and determines corrected defect coordinates of the real defects 74. Concretely, step S14 in FIG. 2 is executed.

In step S32, the processing device 21 of the optical type inspection apparatus 1 determines whether or not the correction period counted by the timer 42 (see FIGS. 1A to 1C) has reached a predetermined period. If the correction period has reached the predetermined period (step S32, Yes), the process returns to step S22, and the correction factors are reset. If the correction period has not reached the predetermined period (step S32, No), the process returns to step S27, and inspection of the mass production wafer 71 is continued. Thus, as the correction factors can be updated either manually or automatically, even in case that the various errors 58-63 change, it is possible to obtain highly accurate corrected defect coordinates by making the coordinate factors follow the change.

DESCRIPTION OF REFERENCE SYMBOLS

1: optical type inspection apparatus (defect inspection device)
11: lighting unit
12: detecting unit
12a: photoreceptive unit
12b: line sensor (image forming unit)
12c: channel
13: stage position detecting unit (Y scale)
14: stage position detecting unit (X scale)
15: lighting device of surface height position detection system
16: detector of surface height position detection system (two detectors for one set: 16a, 16b)
17: image surface observing unit
18: image processing device
19: stage
19a: transporting unit
21: processing device
22: A/D convertor
23: image processing device
24: defect determination device
24a: determination circuit
24b, 24c: factor table
25: stage position detecting unit (coordinate management device)
26: inspection result storage device
27: stage control device
28: image display device
31: coordinate transforming unit
32: difference computing unit
33: characteristic pattern obtaining unit
34: inclination obtaining unit
35: amplitude obtaining unit
36: stage correction factor computing unit
37: channel correction factor computing unit
38: stage correction amount computing unit
39: die correction amount computing unit
40: die coordinate correcting unit
41: storing/transmitting unit
42: timer 51: wafer for coordinates management (wafer)
52: pseudo defect die (chip)
53: die cell
54: pseudo defect
54a: formed image of pseudo defect
55: forward scanning
56: reverse scanning
57: shift
58: defect X coordinate error (inclination error)
59: defect Y coordinate error (magnification ratio error)
61: defect X coordinate error (X scale error)
62: defect Y coordinate error (Y scale error)
63: defect X coordinate error (orthogonal degree error)
71: mass production wafer
72: mass production die
73: die cell
74: real defect
80: inspection system
81: process control section
82: review device
83: transportation system
83a: stocker
Xs: stage X coordinate (stage coordinate)
Ys: stage Y coordinate (stage coordinate)
Xs0: pseudo defect stage X coordinate (pseudo defect stage coordinate)
Ys0: pseudo defect stage Y coordinate (pseudo defect stage coordinate)
Xs1: real defect stage X coordinate (real defect stage coordinate)
Ys1: real defect stage Y coordinate (real defect stage coordinate)
Xd: die X coordinate (die coordinate)
Yd: die Y coordinate (die coordinate)
Xd0: pseudo defect die X coordinate (pseudo defect die coordinate)
Yd0: pseudo defect die Y coordinate (pseudo defect die coordinate)
Xd1: real defect die X coordinate (real defect die coordinate)
Yd1: real defect die Y coordinate (real defect die coordinate)
Xd2: designed X coordinate (designed coordinate)
Yd2: designed Y coordinate (designed coordinate)
ΔX, ΔY: difference
ΔXds, ΔYds: stage correction amount
ΔXdd, ΔYdd: die correction amount
Xdm: corrected real defect die X coordinate (corrected real defect die coordinate)
Ydm: corrected real defect die Y coordinate (corrected real defect die coordinate)
Pd: pitch of pseudo defects
Pds: pitch of formed images of pseudo defects
Pc: pitch of channels
C1-C16: channel
CP1, CP2, CP3: coordinate error characteristic pattern
A1, A2, A3: amplitude (channel correction factor)
L1, L2, L3: line
AL1, AL2, AL3: inclination of line (stage correction factor)

The invention claimed is:

1. An optical type inspection apparatus including a line sensor with plural channels capable of forming an image of a surface of a wafer, the channels being arrayed with equal intervals along Y axis direction, and a transporting unit that forms an image of an entire surface of the wafer on the channels by loading the wafer on a stage and repeatedly transporting, relatively to the line sensor, the wafer along X axis direction perpendicular to the Y axis direction, wherein the optical type inspection apparatus inspects the surface of the wafer, the optical type inspection apparatus comprising:
a stage position detecting unit, wherein,
when a wafer for coordinates management has been arranged such that:
a matrix is set on the surface;
one pseudo defect die is formed on each row of the matrix and one pseudo defect die is formed on each column of the matrix; and
plural pseudo defects are formed in the each pseudo defect die in one array along a column direction with equal intervals such that a pitch between formed images, of the pseudo defects, on the channels is the same as a pitch between the channels,
and if the wafer for coordinates management has been inspected as the wafer such that the Y axis direction and the column direction are substantially parallel to each other and an image of one pseudo defect is formed on the each channel, corresponding to the each pseudo defect die,
then the stage position detecting unit detects a position, on the stage, of the each pseudo defect whose image has been formed on the corresponding channel, as a pseudo defect stage coordinate;
a coordinate transforming unit that transforms the each detected pseudo defect stage coordinate into a pseudo defect die coordinate representing a position in the pseudo defect die that includes the pseudo defect;
a difference computing unit that computes difference of the each pseudo defect die coordinate from a designed coordinate based on design, wherein the difference is generated when the pseudo defect is formed in the corresponding defect die; and
a characteristic pattern obtaining unit that obtains at least either one of a coordinate error characteristic pattern in which the difference vibrates with a substantially constant amplitude with respect to the pseudo defect stage coordinate and a coordinate error characteristic pattern in which the difference increases or decreases along a line.

2. The optical type inspection apparatus according to claim 1, comprising:
an inclination obtaining unit for obtaining inclination of the line; and
a stage correction factor computing unit for computing a stage correction factor that is an error ratio to transportation of the stage, based on the inclination of the line.

3. The optical type inspection apparatus according to claim 2,
wherein when a mass production wafer provided with mass production dies has been inspected as the wafer:
the stage position detecting unit detects as a real defect stage coordinate a position, on the stage, of a real defect on the mass production wafer, an image of the real defect having been formed on the corresponding channel; and
the coordinate transforming unit transforms the detected real defect stage coordinate into a real defect die coordinate that represents a position in the mass production die that includes the real defect;
and wherein the optical type inspection apparatus comprises:
a stage correction amount computing unit for computing a stage correction amount, based on the detected real defect stage coordinate and the stage correction factor;

a die coordinate correcting unit for correcting the real defect die coordinate, based on the stage correction amount; and a storing/transmitting unit for storing the corrected real defect die coordinate or transmitting the corrected real defect die coordinate to outside.

4. An inspection system, comprising:

the optical type inspection apparatus according to claim 3; and a review device that receives the corrected real defect die coordinate, and displays, with magnification, periphery of the corrected real defect die coordinate in the mass production die corresponding to the corrected real defect die coordinate.

5. The optical type inspection apparatus according to claim 2, comprising:

an amplitude obtaining unit for obtaining magnitude of the amplitude; and a channel correction factor computing unit for computing a channel correction factor that is a ratio of error caused by the channels to the pitch between the channels, based on the magnitude of the amplitude.

6. The optical type inspection apparatus according to claim 1, comprising:

an amplitude obtaining unit for obtaining magnitude of the amplitude; and a channel correction factor computing unit for computing a channel correction factor that is a ratio of error caused by the channels to the pitch between the channels, based on the magnitude of the amplitude.

7. The optical type inspection apparatus according to claim 6, wherein when a mass production wafer provided with mass production dies has been inspected as the wafer:

the stage position detecting unit detects as a real defect stage coordinate a position, on the stage, of a real defect on the mass production wafer, an image of the real defect having been formed on the corresponding channel; and the coordinate transforming unit transforms the detected real defect stage coordinate into a real defect die coordinate that represents a position in the mass production die that includes the real defect;

and wherein the optical type inspection apparatus comprises:

a die correction amount computing unit for computing a die correction amount, based on the detected real defect die coordinate and the stage correction factor;

a die coordinate correcting unit for correcting the real defect die coordinate, based on the die correction amount; and a storing/transmitting unit for storing the corrected real defect die coordinate or transmitting the corrected real defect die coordinate to outside.

8. An inspection system, comprising:

the optical type inspection apparatus according to claim 7; and a review device that receives the corrected real defect die coordinate, and displays, with magnification, periphery of the corrected real defect die coordinate in the mass production die corresponding to the corrected real defect die coordinate.

9. The optical type inspection apparatus according to claim 1, wherein the pseudo defect stage coordinate includes a pseudo defect stage X coordinate based on a coordinate axis that is parallel with the X axis direction, wherein the pseudo defect die coordinate includes a pseudo detect die X coordinate that is transformed from the pseudo defect stage X coordinate and based on a coordinate axis that is parallel with the X axis direction, wherein the designed coordinate includes a designed X coordinate based on the coordinate axis that is parallel with the X axis direction, wherein the difference is generated in a direction parallel with the X axis direction, and wherein the coordinate error characteristic pattern is at least either one of a coordinate error characteristic pattern in which the difference vibrates along the X axis direction with the amplitude, accompanying an increase in the pseudo defect stage X coordinate, and a coordinate error characteristic pattern in which the difference increases or decreases along the line in the X axis direction, accompanying the increase in the pseudo defect stage X coordinate.

10. The optical type inspection apparatus according to claim 9, wherein the pseudo defect stage coordinate includes a pseudo defect stage Y coordinate based on a coordinate axis that is parallel with the Y axis direction, wherein the pseudo defect die coordinate includes a pseudo detect die Y coordinate that is transformed from the pseudo defect stage Y coordinate and based on a coordinate axis that is parallel with the Y axis direction, wherein the designed coordinate includes a designed Y coordinate based on the coordinate axis that is parallel with the Y axis direction, wherein the difference is generated in a direction parallel with the Y axis direction, and wherein the coordinate error characteristic pattern is at least either one of a coordinate error characteristic pattern in which the difference vibrates along the Y axis direction with the amplitude, accompanying an increase in the pseudo defect stage Y coordinate, and a coordinate error characteristic pattern in which the difference increases or decreases along the line in the Y axis direction, accompanying the increase in the pseudo defect stage Y coordinate.

11. The optical type inspection apparatus according to claim 1, wherein the pseudo defect stage coordinate includes a pseudo defect stage Y coordinate based on a coordinate axis that is parallel with the Y axis direction, wherein the pseudo defect die coordinate includes a pseudo detect die Y coordinate that is transformed from the pseudo defect stage Y coordinate and based on a coordinate axis that is parallel with the Y axis direction, wherein the designed coordinate includes a designed Y coordinate based on the coordinate axis that is parallel with the Y axis direction, wherein the difference is generated in a direction parallel with the Y axis direction, and wherein the coordinate error characteristic pattern is at least either one of a coordinate error characteristic pattern in which the difference vibrates along the Y axis direction with the amplitude, accompanying an increase in the pseudo defect stage Y coordinate, and a coordinate error characteristic pattern in which the difference increases or decreases along the line in the Y axis direction, accompanying the increase in the pseudo defect stage Y coordinate.

12. The optical type inspection apparatus according to claim 1, wherein the pseudo defect stage coordinate includes a pseudo defect stage Y coordinate based on a coordinate axis that is parallel with the Y axis direction and a pseudo defect stage X coordinate based on a coordinate axis that is parallel with the X axis direction, wherein the pseudo defect die coordinate includes a pseudo detect die X coordinate that is transformed from the pseudo defect stage X coordinate and based on a coordinate axis that is parallel with the X axis direction, wherein the designed coordinate includes a designed X coordinate based on the coordinate axis that is parallel with the X axis direction, wherein the difference is generated in a direction that is parallel with the X axis direction, and wherein the coordinate error characteristic pattern is at least either one of a coordinate error characteristic pattern in which the difference vibrates along the X axis direction with the amplitude, accompanying an increase in the pseudo defect stage Y coordinate, and a coordinate error characteristic pattern in which the difference increases or decreases along the line in the X axis direction, accompanying the increase in the pseudo defect stage Y coordinate.

13. A wafer for coordinates management, wherein a matrix is set on a surface of the wafer for coordinates management, wherein only one pseudo defect die is formed on each row of the matrix and only one pseudo defect die is formed on each column of the matrix, and wherein plural pseudo defects are formed on the each pseudo defect die with equal intervals only in one array along column direction of the matrix.

* * * * *